United States Patent
Ohkawa et al.

[11] Patent Number: 5,922,771
[45] Date of Patent: Jul. 13, 1999

[54] BENZOCYCLOALKENE COMPOUNDS, THEIR PRODUCTION AND USE

[75] Inventors: Shigenori Ohkawa, Osaka; Osamu Uchikawa, Hyogo; Kohji Fukatsu, Hyogo; Masaomi Miyamoto, Hyogo, all of Japan

[73] Assignee: Takeda Chemical Industries, Ltd., Osaka, Japan

[21] Appl. No.: 08/693,058

[22] PCT Filed: Jul. 25, 1996

[86] PCT No.: PCT/JP96/02091

§ 371 Date: Aug. 19, 1996

§ 102(e) Date: Aug. 19, 1996

[87] PCT Pub. No.: WO97/05098

PCT Pub. Date: Feb. 13, 1997

[30] Foreign Application Priority Data

Jul. 26, 1995 [JP] Japan ................................. 7-190830

[51] Int. Cl.[6] ..................... C07D 317/70; C07C 233/64; C07C 235/00; C07C 237/00; A61K 31/335; A61K 31/27; A61K 31/165; A61K 31/16

[52] U.S. Cl. .................... 514/630; 549/349; 549/359; 549/433; 560/28; 564/56; 564/163; 564/166; 564/167; 564/168; 564/169; 564/170; 564/171; 564/172; 564/174; 564/176; 564/179; 564/180; 564/181; 564/185; 564/188; 564/189; 564/190; 564/191; 564/192; 564/196; 564/200; 564/202; 564/207; 564/212; 564/213; 564/219; 564/220; 514/450; 514/452; 514/463; 514/480; 514/481; 514/595; 514/617; 514/619; 514/620; 514/621; 514/622; 514/624; 514/625; 514/626; 514/627; 514/628; 514/629

[58] Field of Search ..................... 549/349, 359, 549/433; 560/28; 564/56, 163, 166, 167, 168, 169, 170, 171, 172, 174, 176, 179, 180, 181, 185, 188, 189, 190, 191, 192, 196, 200, 202, 207, 212, 213, 219, 220; 514/450, 452, 463, 480, 481, 595, 617, 619, 620, 621, 622, 624, 625, 626, 627, 628, 629, 630

[56] References Cited

U.S. PATENT DOCUMENTS 3,642,785  2/1972  Shen et al. .................... 260/240 R
4,656,190  4/1987  Shen et al. .................... 514/529
5,158,948  10/1992 Schoenleber et al. ........... 514/213
5,194,614  3/1993  Andrieux et al. ............... 544/400
5,308,866  5/1994  Lesieur et al. .................. 514/469
5,668,180  9/1997  Lesieur et al. .................. 514/630
5,731,352  3/1998  Lesieur et al. .................. 514/630

FOREIGN PATENT DOCUMENTS 0420064  4/1991  European Pat. Off. .
0447285  9/1991  European Pat. Off. .
0527687  1/1993  European Pat. Off. .
0721938  7/1996  European Pat. Off. .
0721947  7/1996  European Pat. Off. .
WO 08466  3/1996  WIPO .

OTHER PUBLICATIONS

J. Chem. Soc., C.(1971) 3506–3510.
Tetrahedron Letters, No. 25 (1969) 2085–2088.
Mathe–Allainmat et al., Recent Developments in Melatonin Receptor Ligands, Expert Opinion on Therapeutic Patents, vol. 7, No. 12, pp. 1447–1458, Dec. 1997.

Primary Examiner—Richard L. Raymond
Assistant Examiner—Brenda Coleman
Attorney, Agent, or Firm—Fitzpatrick, Cella, Harper & Scinto

[57] ABSTRACT

A compound of the formula

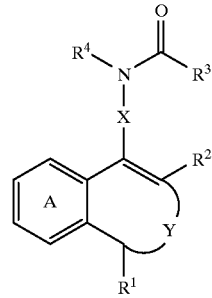

wherein $R^1$ and $R^2$ independently represent H or an optionally substituted hydrocarbon group; $R^3$ represents an optionally substituted hydrocarbon group; $R^4$ represents H or a hydrocarbon group; ring A represents a substituted benzene ring; X represents a $C_{2-4}$ alkylene group etc.; and Y represents a bond or a lower alkylene group, or salts thereof is useful as prophylactic or therapeutic agents of diseases related with melatonin activity.

19 Claims, No Drawings

BENZOCYCLOALKENE COMPOUNDS, THEIR PRODUCTION AND USE

This application is a 371 of PCT/JP96/02091, filed Jul. 25, 1996.

TECHNICAL FIELD

This invention relates to novel benzocycloalkene compounds having an excellent binding affinity for melatonin receptor, process for producing them and use.

BACKGROUND ART

Melatonin (N-acetyl-5-methoxytryptamine), which is a hormone synthesized and secreted principally in the pineal gland, increases in dark circumstances and decreases in light circumstances. Further, melatonin exerts suppressively on pigment cells or female gonad and acts as a synchronous factor of biological clock while taking part in transmittance of photoperiodic code. Therefore, melatonin is expected to have use for therapy of diseases related with melatonin activity, such as reproduction and endocrinic disorders, sleep-awake rhythm disorders, jet lag syndrome and various disorders related to aging. Recently it has also been clarified that production of melatonin decreases as aging proceeds, and there is a report in Ann. N.Y. Acad. Sci., Vol.719, pp.456–460 (1994) that maintaining the production of melatonin can intervene in the aging process. However, "Bioorganic & Medicinal Chemistry Letters, Vol.4, p.1485(1994)" describes that when the action on central nervous system is expected, melatonin is shown to be inactive by peripheral administration because melatonin itself has poor intracerebral transferability. There is also reported in "Rinsho Kensa Vol.38, No.11, 1994" that melatonin is readily metabolized by metabolic enzyme in a living body. As a melatonin-agonistic substance, there are reported naphthalene derivatives, for example N-[2-(7-methoxynaphth-1-yl) ethyl]acetamide, represented by the formula:

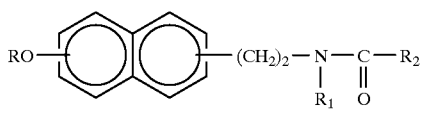

wherein $R_1$ represents e.g. H and lower alkyl, and $R_2$ represents e.g. H and an optionally halogenated lower alkyl (JP-A-7-48331, EP-A-447285), and tetrahydronaphthalene derivatives having acylamino group substituted at the 2-position of tetrahydrofuran (JP-A-3-169840, EP-A-420064).

On the other hand, as examples of a benzocycloalkene compound having endo double bond, the following compounds have been known.

1) As an intermediate of synthesizing steroid, compounds represented by the formula:

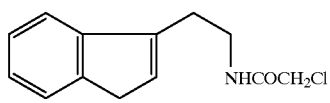

are described in Tetrahedron Lett., p.2085(1969).

2) Compounds represented by the formula:

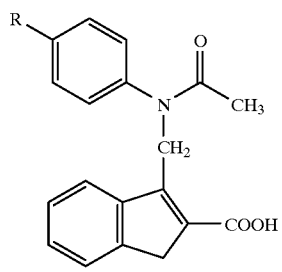

wherein R represents $CH_3$, Cl and $NO_2$ are described in J. Chemi. Soc. (C), p.3506, (1971). No description on the use of these compounds are given.

3) As an intermediate of tetracyclic spirobenzazepine having a dopamine receptor antagonistic activity, compounds represented by the formula:

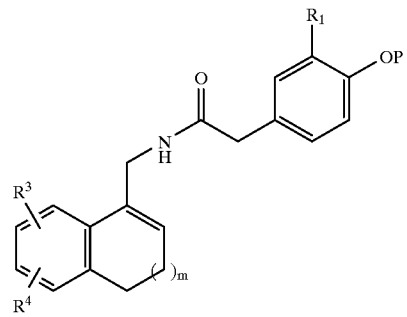

wherein $R^1$ represents e.g. H and an alkyl group, $R^3$ and $R^4$ represent e.g. H and a lower alkoxy group, P represents a protective group and m denotes 0 to 2 are described in U.S. Pat. No. 5,158,948.

4) Compounds, having antibacterial and antiinflammatory activities, represented by the formula:

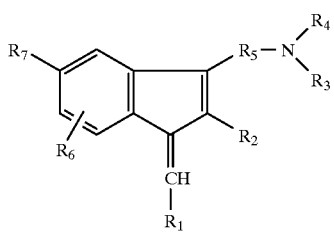

wherein $R_1$ represents e.g. aryl, $R_2$ represents e.g. H and aryl, $R_3$ represents e.g. H, $R_4$ represents e.g. acyl, $R_5$ represents lower alkyl, $R_6$ represents e.g. H, and $R_7$ represents e.g. H and lower alkoxy are described in U.S. Pat. No. 3,642,785.

5) Compounds, having platelet activating factor antagonistic activity, represented by the formula:

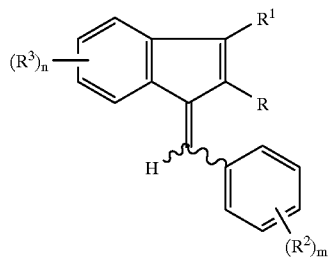

wherein $R^1$ represents H and lower alkyl, $R^2$ represents e.g. —$CH_2$—$CONRR^4$, $R^4$ represents H and lower alkyl, $R^3$ represents e.g. lower alkoxy, m denotes 1 to 4, and n denotes 1, 2 or 3 are described in U.S. Pat. No. 4,656,190.

However, no reports have been made on the relation of these compounds with a melatonin receptor.

A melatonin agonist, which is different from melatonin in the structure, has an excellent affinity for melatonin receptor, and has excellent transferability into brain and metabolic stability, is expected to show therapeutic effects superior to those of melatonin. At the present circumstances, no compounds which are fully satisfactory in the activities of melatonin receptors, in metabolic stability and in transferability into brain have been found. So development of suitable compounds, which are different from the above-mentioned known compounds in chemical structure, have excellent melatonin receptor agonistic activities and are fully satisfactory as medicines, is ardently desired.

DISCLOSURE OF INVENTION

The present inventors succeeded, for the first time, in creation of the novel compound represented by the following formula (I), whose characteristic feature of the chemical structure lies in having a carbonylamino $C_{2-4}$ alkyl group at the endo double bond conjugated with the benzene ring of benzocycloalkene of the formula:

wherein m represents an integer of 0 to 2 and ring A is defined as below, represented by the formula:

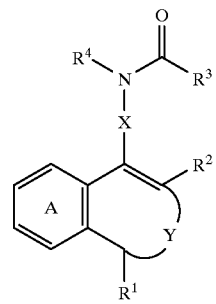

wherein $R^1$ represents hydrogen or an optionally substituted hydrocarbon group; $R^2$ represents hydrogen, an optionally substituted hydrocarbon group or an optionally substituted heterocyclic group; $R^3$ represents an optionally substituted hydrocarbon group, an optionally substituted amino group or a substituted hydroxyl group; $R^4$ represents hydrogen or an optionally substituted hydrocarbon group; ring A represents a substituted benzene ring; X represents an optionally substituted $C_{2-4}$ alkylene group; and Y represents a bond or an optionally substituted lower alkylene group, or a salt thereof [hereinafter sometimes referred to as Compound (I)], and further found that the compound ($I^a$) represented by the formula:

($I^a$)

wherein ......... represents a single bond or a double bond; $R^{1a}$ represents hydrogen or an optionally substituted hydrocarbon group; ring $A^a$ represents an optionally substituted benzene ring; $X^a$ represents an optionally substituted lower alkylene group, and other symbols are as defined above, including the compound (I), or a salt thereof, have excellent properties as melatonin agonist, e.g. binding affinity for melatonin receptor, and are satisfactory as medicines. Based on these findings, the present inventors have completed the invention.

More specifically, this invention relates to
(1) the compound (I),
(2) the compound of the above (1) wherein $R^1$ is i) hydrogen or ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxyl, $C_{1-6}$ alkoxy, $C_{1-6}$ alkyl, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, $R^2$ is (i) hydrogen, (ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxyl, $C_{1-6}$ alkoxy, $C_{1-6}$ alkyl, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy or iii) a 5- to 10-membered heterocyclic group containing, besides carbon atoms, 1 to 4 hetero atoms selected from nitrogen atom, oxygen atom and sulfur atom, which group may be substituted by 1 to 5 substituents selected from the group consisting of a halogen, $C_{1-6}$ alkyl, $C_{3-6}$ cycloalkyl, $C_{2-6}$ alkynyl, $C_{2-6}$ alkenyl, $C_{7-11}$ arallkyl, $C_{6-10}$ aryl, $C_{1-6}$ alkoxy, $C_{6-10}$ aryloxy, $C_{1-6}$ alkyl-carbonyl, $C_{6-10}$ aryl-carbonyl, $C_{1-6}$ alkyl-carbonyloxy, $C_{6-10}$ aryl-carbonyloxy, carboxyl, $C_{1-6}$ alkoxy-carbonyl, carbamoyl, mono-, di- or tri-halogeno-$C_{1-4}$ alkyl, oxo, amidino, imino, amino, mono-$C_{1-6}$ alkylamino, di-$C_{1-6}$ alkylamino, 3- to 6-membered cyclic amino, $C_{1-3}$ alkylenedioxy, hydroxyl, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl, $R^3$ is (i) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxyl, $C_{1-6}$ alkoxy, $C_{1-6}$ alkyl, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, (ii) an amino group which may be substituted by 1 or 2 substituents selected from the group consisting of a $C_{1-6}$ alkyl, $C_{2-6}$ alkenyl, $C_{2-6}$ alkynyl, $C_{3-6}$ cycloalkyl and $C_{6-14}$ aryl group, each of which may be substituted by 1 to 5 substituents selected from the group consisting of a halogen, nitro, cyano, hydroxyl, $C_{1-6}$ alkoxy, $C_{1-6}$ alkyl, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy or (iii) a hydroxyl group substituted by a $C_{1-6}$ alkyl, $C_{2-6}$ alkenyl, $C_{2-6}$ alkynyl, $C_{3-6}$ cycloalkyl or $C_{6-14}$ aryl group, each of which may be substituted by 1 to 5 substituents selected from the group consisting of a halogen, nitro, cyano, hydroxyl, $C_{1-6}$ alkoxy, $C_{1-6}$ alkyl, amino, mono-$C_{1-6}$ alkylamino, di-$C_{1-6}$ alkylamino, carboxyl, $C_{1-6}$ alkylcarbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, $R^4$ is (i) hydrogen or (ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxyl, $C_{1-6}$ alkoxy, $C_{1-6}$ alkyl, amino, mono-$C_{1-6}$ alkylamino, di-$C_{1-6}$ alkylamino, carboxyl, $C_{1-6}$ alkylcarbonyl, $C_{1-6}$ alkoxycarbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, ring A is a benzene ring substituted by 1 to 3 substituents selected from the group consisting of (i) halogen, (ii) hydroxyl, (iii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxyl, $C_{1-6}$ alkoxy, $C_{1-6}$ alkyl, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbanoyl, $C_{6-10}$ aryl and $C_{6-10}$ aryloxy, (iv) an amino group which may be substituted by 1 or 2 substituents selected from the group consisting of a $C_{1-6}$ alkyl, $C_{2-6}$ alkenyl, $C_{2-6}$ alkynyl, $C_{3-6}$ cycloalkyl and $C_{6-14}$ aryl group, each of which may be substituted by 1 to 5 substituents selected from the group consisting of a halogen, nitro, cyano, hydroxyl, $C_{1-6}$ alkoxy, $C_{1-6}$ alkyl, amino, mono-$C_{1-6}$ alkylamino, di-$C_{1-6}$ alkxylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, (v) a mercapto group which may be substituted by a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxyl, $C_{1-6}$ alkoxy, $C_{1-6}$ alkyl, amino, mono-$C_{1-6}$ alkylamino, di-$C_{1-6}$ alkylamino, carboxyl, $C_{1-6}$ alkylcarbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, (vi) a hydroxyl group substituted by a $C_{1-6}$ alkyl, $C_{2-6}$ alkenyl, $C_{2-6}$ alkynyl, $C_{3-6}$ cycloalkyl or $C_{6-14}$ aryl group, each of which may be substituted by 1 to 5 substituents selected from the group consisting of a halogen, nitro, cyano, hydroxyl, $C_{1-6}$ alkoxy, $C_{1-6}$ alkyl, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, (vii) a $C_{1-6}$ acylamino group and (viii) a $C_{1-3}$ alkylenedioxy group, X is a straight $C_{2-4}$ alkylene group which may be substituted by 1 to 3 substituents selected from the group consisting of (i) a $C_{1-6}$ alkyl, $C_{2-6}$ alkenyl, $C_{2-6}$ alkynyl, $C_{3-6}$ cycloalkyl or $C_{6-14}$ aryl group, each of which may be substituted by 1 to 5 substituents selected from the group consisting of a halogen, nitro, cyano, hydroxyl, $C_{1-6}$ alkoxy, $C_{1-6}$ alkyl, amino, mono-$C_{1-6}$ alkylamino, di-$C_{1-6}$ alkylamino, carboxyl, $C_{1-6}$ alkylcarbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, (ii) halogen, (iii) nitro, (iv) cyano, (v) hydroxyl, (vi) $C_{1-6}$ alkoxy, (vii) amino, (viii) mono-$C_{1-6}$ alkylamino, (ix) di-$C_{1-6}$ alkylamino, (x) $C_{1-6}$ alkylcarbonyl and (xi) $C_{6-10}$ aryloxy, and Y is a bond or a straight $C_{1-3}$ alkylene group which may be substituted by 1 to 3 substituents selected from the group consisting of (i) a $C_{1-6}$ alkyl, $C_{2-6}$ alkenyl, $C_{2-6}$ alkynyl, $C_{3-6}$ cycloalkyl or $C_{6-14}$ aryl group, each of which may be substituted by 1 to 5 substituents selected from the group consisting of a halogen, nitro, cyano, hydroxyl, $C_{1-6}$ alkoxy, $C_{1-6}$ alkyl, amino, mono-$C_{1-6}$ alkylamino, di-$C_{1-6}$ alkylamino, carboxyl, $C_{1-6}$ alkylcarbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, (ii) halogen, (iii) nitro, (iv) cyano, (v) hydroxyl, (vi) $C_{1-6}$ alkoxy, (vii) amino, (viii) mono-$C_{1-6}$ alkylamino, (ix) di-$C_{1-6}$ alkylamino, (x) $C_{1-6}$ alkylcarbonyl and (xi) $C_{6-10}$ aryloxy, (3) the compound of the above (2) wherein $R^1$ is hydrogen or a $C_{1-6}$ alkyl group, (4) the compound of the above (2) wherein $R^2$ is (i) hydrogen, (ii) a $C_{6-14}$ aryl group which may be substituted by 1 to 5 substituents selected from the group consisting of a halogen, nitro, cyano, hydroxyl, $C_{1-6}$ alkoxy, $C_{1-6}$ alkyl, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy or (iii) a 5- or 6-membered heteroaromatic group which may be substituted by 1 to 3 substituents selected from the group consisting of a halogen, $C_{1-6}$ alkyl, $C_{3-6}$ cycloalkyl, $C_{2-6}$ alkynyl, $C_{2-6}$ alkenyl, $C_{7-11}$ aralkyl, $C_{6-10}$ aryl, $C_{1-6}$ alkoxy, $C_{6-10}$ aryloxy, $C_{1-6}$ alkyl-carbonyl, $C_{6-10}$ aryl-carbonyl, $C_{1-6}$ alkyl-carbonyloxy, $C_{6-10}$ arylcarbonyloxy, carboxyl, $C_{1-6}$ alkoxy-carbonyl, carbamoyl, mono-, di- or tri-halogeno-$C_{1-4}$ alkyl, oxo, amidino, imino, amino, mono-$C_{1-6}$ alkylamino, di-$C_{1-6}$ alkylamino, 3- to 6-membered cyclic amino, $C_{1-3}$ alkylenedioxy, hydroxyl, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl, (5) the compound of the above (2) wherein $R^3$ is a $C_{1-6}$ alkyl group which may be substituted by 1 to 5 substituents selected from the group consisting of a halogen, nitro, cyano, hydroxyl, $C_{1-6}$ alkoxy, $C_{1-6}$ alkyl, Gamino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, di-$C_{6-10}$ arylcarbamoyl, $C_{6-10}$ aryl and $C_{6-10}$ aryloxy, (6) the compound of the above (2) wherein $R^4$ is hydrogen or a $C_{1-6}$ alkyl group, (7) the compound of the above (2) wherein ring A is a benzene ring substituted by 1 or 2 substituents selected from the group consisting of halogen and a $C_{1-6}$ alkoxy group, (8) the compound of the above (2) wherein ring A moiety is represented by the formula:

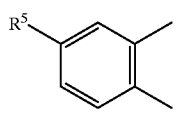

wherein $R^5$ represents a $C_{1-6}$ alkoxy group, (9) the compound of the above (2) wherein X is an ethylene group,

(10) the compound of the above (2) wherein Y is a bond or a methylene group,

(11) the compound of the above (1) wherein $R^1$ is hydrogen; $R^2$ is (i) hydrogen or (ii) a $C_{6-14}$ aryl or 5- or 6-membered heteroaromatic group which may be substituted by 1 to 3 substituents selected from the group consisting of a halogen, $C_{1-6}$ alkoxy, $C_{1-6}$ alkyl and $C_{6-10}$ aryl; $R^3$ is a $C_{1-6}$ alkyl group which may be substituted by 1 to 3 halogens; $R^4$ is hydrogen; ring A is a benzene ring substituted by 1 or 2 substituents selected from the group consisting of halogen and a $C_{1-6}$ alkoxy group; X is an ethylene group; and Y is a bond or a methylene group,

(12) the compound of the above (1) wherein $R^1$ is hydrogen; $R^2$ is hydrogen, a $C_{6-10}$ aryl group or a $C_{6-10}$ aryl-$C_{1-4}$ alkyl group; $R^3$ is a $C_{1-6}$ alkyl group which may be substituted by 1 to 3 halogens; $R^4$ is hydrogen; ring A is a benzene ring substituted by 1 or 2 substituents selected from the group consisting of halogen and a $C_{1-6}$ alkoxy group; X is a $C_{2-4}$ alkylene group; and Y is a bond or a methylene group,

(13) the compound of the above (1) which is 2,2,2-trifluoro-N-[2-(5-methoxy-2-phenyl-1H-inden-3-yl)ethyl]acetamide,
N-[2-(5-methoxy-1H-inden-3-yl)ethyl]propionamide, or
N-[2-(5-methoxy-1H-inden-3-yl)ethyl]butyramide,

(14) a process for producing the compound of the above (1), which comprises reacting a compound of (i) the formula:

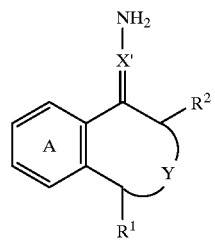

wherein X' represents a trivalent group formed by removing one hydrogen atom from the group represented by X in the above (1), and other symbols are as defined above or (ii) the formula:

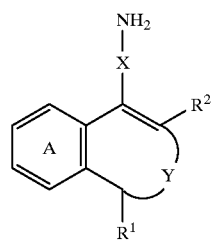

wherein all symbols are as defined above, or a salt thereof, with a carboxylic acid, a salt or a reactive derivative thereof or with an isocyanate,

(15) a pharmaceutical composition which comprises a compound of the above (1), if necessary together with a pharmaceutically acceptable carrier,

(16) the composition of the above (15) which has a binding affinity for melatonin receptor,

(17) the composition of the above (16) which is a regulating agent of circadian rhythm,

(18) the composition of the above (16) which is a regulating agent of sleep-awake rhythm,

(19) the composition of the above (16) which is a regulating agent of time zone change syndrome,

(20) the composition of the above (15) which is a therapeutic agent of sleep disorders,

(21) a composition having a binding affinity for melatonin receptor which comprises a compound represented by the formula (I$^a$) or a salt thereof, and

(22) the composition of the above (21), which is a melatonin receptor agonistic composition.

Examples of "hydrocarbon groups" of "optionally substituted hydrocarbon groups" shown by $R^1$, $R^2$, $R^3$, $R^4$ or $R^{1a}$ in the above-mentioned formulae include, for example, aliphatic hydrocarbon groups, monocyclic saturated hydrocarbon groups and aromatic hydrocarbon groups. The carbon number of the hydrocarbon group is preferably 1 to 16. Alkyl groups, alkenyl groups, alkynyl groups, cycloalkyl groups and aryl groups are exemplified.

"Alkyl group" is preferably a lower alkyl group, for example, $C_{1-6}$ alkyl groups such as methyl, ethyl, propyl, isopropyl, butyl, isobutyl, sec-butyl, tert-butyl, pentyl and hexyl.

"Alkenyl group" is preferably a lower alkenyl group, for example, $C_{2-6}$ alkenyl groups such as vinyl, allyl, isopropenyl, butenyl and isobutenyl.

"Alkynyl group" is preferably a lower alkynyl group, for example, $C_{2-6}$ alkynyl groups such as ethynyl, 1-propynyl and propargyl.

"Cycloalkyl group" is preferably a lower cycloalkyl group, for example, $C_{3-6}$ cycloalkyl groups such as cyclopropyl, cyclobutyl, cyclopentyl and cyclohexyl.

"Aryl group", is, for example, $C_{6-14}$ aryl groups such as phenyl, 1-naphthyl, 2-naphthyl, biphenylyl, 2-indenyl and 2-anthryl. Among these, phenyl group is preferably employed.

Incidentally, when $R^{1a}$ bonded to the ring through the double bond, $R^{1a}$ represents a divalent group formed by removing one hydrogen atom from the above-mentioned "optionally substituted hydrocarbon group".

Examples of the substituents, which "hydrocarbon group" of "optionally substituted hydrocarbon group" shown by $R^1$, $R^2$, $R^3$, $R^4$ or $R^{1a}$ may optionally have, include, for example, halogen atoms (e.g. fluorine, chlorine, bromine and iodine), nitro group, cyano group, hydroxyl group, a lower alkoxy group (e.g. $C_{1-6}$ alkoxy groups such as methoxy, ethoxy, propoxy, isopropoxy, butoxy, isobutoxy, pentyloxy and hexyloxy), a lower alkyl group (e.g. $C_{1-6}$ alkyl groups such as methyl, ethyl, propyl, isopropyl, butyl, isobutyl, sec-butyl, tert-butyl, pentyl and hexyl), amino group, mono-lower alkylamino group (e.g. mono-$C_{1-6}$ alkylamino groups such as methylamino and ethylamino), di-lower alkylamino group (e.g. di-$C_{1-6}$ alkylamino groups such as dimethylamino, diethylamino and methylethylamino), carboxyl group, lower alkylcarbonyl group (e.g. $C_{1-6}$ alkylcarbonyl groups such as acetyl and propionyl), lower alkoxycarbonyl group (e.g. $C_{1-6}$ alkoxy-carbonyl groups such as methoxycarbonyl, ethoxycarbonyl, propoxycarbonyl and butoxycarbonyl), carbamoyl group, mono-lower alkylcarbamoyl group (e.g. mono-$C_{1-6}$ alkylcarbamoyl groups such as methylcarbamoyl and ethylcarbamoyl), a di-lower alkylcarbamoyl group (e.g. di-$C_{1-6}$ alkylcarbamoyl groups such as dimethylcarbamoyl and diethylcarbamoyl), mono-arylcarbamoyl group (e.g. mono-$C_{6-10}$ arylcarbamoyl groups such as phenylcarbamoyl and naphthylcarbamoyl), di-arylcarbamoyl group (e.g. di-$C_{6-10}$ arylcarbamoyl groups such as diphenylcarbamoyl) aryl group (e.g. $C_{6-10}$ aryl groups such as phenyl and naphthyl), and aryloxy group (e.g. $C_{6-10}$ aryloxy groups such as phenyloxy and napthyloxy).

The "hydrocarbon group" of the "optionally substituted hydrocarbon group" may optionally have 1 to 5, preferably 1 to 3 of the above-mentioned substituents at any possible position. Additionally, when the number of the substituent is two or more, each substituent may be selected independently, that is, the same as or different from one another. "Heterocyclic group" of "optionally substituted heterocyclic group" shown by $R^2$ include, for example, a 5- to 10-membered (monocyclic or condensed dicyclic) heterocyclic group containing, besides carbon atoms, one or two species, preferably 1 to 4 hetero atoms selected from nitrogen atom, oxygen atom and sulfur atom. Examples of the heterocyclic group include a 5-membered heterocyclic group containing, besides carbon atoms, 1 to 4 hetero atoms selected from oxygen atom, sulfur atom and nitrogen atom, such as 2- or 3-thienyl, 2- or 3-furyl, 1-, 2- or 3-pyrrolyl, 1- 2- or 3-pyrrolidinyl, 2-, 4- or 5-oxazolyl, 2-, 4- or 5-thiazolyl, 3-, 4- or 5-pyrazolyl, 2-, 4- or imidazolyl, 1,2,3-triazolyl, 1,2,4-triazolyl, and 1H- or 2H-tetrazolyl; a 6-membered heterocyclic group containing, besides carbon atoms, 1 to 4 hetero atoms selected from oxygen atom, sulfur atom and nitrogen atom, such as 2-, 3- or 4-pyridyl, 2-, 4- or 5-pyrimidinyl, thiomorpholinyl, morpholinyl, piperidinyl, pyranyl, thiopyranyl, 1,4-oxazinyl, 1,4-thiazinyl, 1,3-thiazinyl, piperazinyl, triazinyl, 3- or 4-pyridazinyl and pyrazinyl; a condensed dicyclic or tricyclic group containing, besides carbon atoms, 1 to 4 hetero atoms selected from oxygen atom, sulfur atom and nitrogen atom, such as indolyl, benzofuryl, benzothiazolyl, benzoxazolyl, benzimidazolyl, quinolyl, isoquinolyl, phthalazinyl, quinazolynyl, quinoxalinyl, indolizinyl, quinolizinyl, 1,8-naphthyridinyl, dibenzofuranyl, carbazolyl, acridinyl, phenanthridinyl chromanyl, phenothiazinyl and phenoxazinyl (preferably, groups in which the above 5- or 6-membered heterocyclic group condensing with one or two 5- to 6-membered cyclic groups optionally containing, besides carbon atoms, 1 to 4 hetero atoms selected from oxygen atom, sulfur atom and nitrogen atom). Among others, preferred is a 5- or 6-membered heteroaromatic group optionally condensing with one benzene ring such as 2-, 3- or 4-pyridyl, 2- or 3-thienyl, 1-, 2- or 3-indolyl and 2-, 3-, 4-, 5- or 8-quinolyl.

Examples of the substituents, which "heterocyclic group" of "optionally substituted heterocyclic group" represented by $R^2$ may optionally have, include, for example, halogen atoms (e.g. fluorine, chlorine, bromine and iodine), lower allkyl group (e.g. $C_{1-6}$ alkyl groups such as methyl, ethyl, propyl, isopropyl, butyl, isobutyl, sec-butyl and tert-butyl), cycloalkyl group (e.g. $C_{3-6}$ cycloalkyl groups such as cyclopropyl, cyclobutyl, cyclopentyl and cyclohexyl), lower alkynyl group (e.g. $C_{2-6}$ alkynyl groups such as ethynyl, 1-propynyl and propargyl), lower alkenyl group (e.g. $C_{2-6}$ alkenyl groups such as vinyl, allyl, isopropenyl, butenyl and isobutenyl), aralkyl group (e.g. $C_{7-11}$ aralkyl groups such as benzyl, α-methylbenzyl and phenethyl), aryl group (e.g. $C_{6-10}$ aryl groups such as phenyl and naphthyl, preferably phenyl group), lower alkoxy group (e.g. $C_{1-6}$ alkoxy groups such as methoxy, ethoxy, propoxy, isopropoxy, butoxy, isobutoxy, sec-butoxy and tert-butoxy), aryloxy group (e.g. $C_{6-10}$ aryloxy groups such as phenoxy), lower alkanoyl group (e.g. $C_{1-6}$ alkyl-carbonyl groups such as acetyl, propionyl, butyryl and isobutyryl), arylcarbonyl group (e.g. $C_{6-10}$ aryl-carbonyl groups such as benzoyl and naphthoyl), lower alkanoyloxy group (e.g. $C_{1-6}$ alkyl-carbonyloxy groups such as acetyloxy, propionyloxy, butyryloxy and isobutyryloxy), arylcarbonyloxy group (e.g. $C_{6-10}$ arylcarbonyloxy groups such as benzoyloxy and naphthoyloxy), carboxyl group, lower alkoxycarbonyl group (e.g. $C_{1-6}$ alkoxy-carbonyl groups such as methoxycarbonyl, ethoxycarbonyl, propoxycarbonyl, isopropoxycarbonyl, butoxycarbonyl, isobutoxycarbonyl and tert-butoxycarbonyl), carbamoyl group, mono- di- or tri-halogeno-lower alkyl group (e.g. mono-, di- or tri-halogeno-$C_{1-4}$ alkyl groups such as chloromethyl, dichloromethyl, trifluoromethyl and trifluoroethyl), oxo group, amidino group, imino group, mono-lower alkylamino group (e.g. mono-$C_{1-6}$ alkylamino groups such as methylamino, ethylamino, propylamino, isopropylamino and butylamino), di-lower alkylamino group (e.g. di-$C_{1-6}$ alkylamino groups such as dimethylamino, diethylamino, methylethylamino, dipropylamino, diisopropylamino and dibutylamino), 3- to 6-membered cyclic amino group optionally containing, besides carbon atoms and one nitrogen atom, 1 to 3 hetero atoms selected from oxygen atom, sulfur atom and nitrogen atom (e.g. 3- to 6-membered cyclic amino groups such as aziridinyl, azetidinyl, pyrrolidinyl, pyrrolinyl, pyrrolyl, imidazolyl, pyrazolyl, imidazolidinyl, piperidino, morpholino, dihydropyridyl, pyridyl, N-methylpiperazinyl and N-ethylpiperazinyl), alkylenedioxy group (e.g. $C_{1-3}$ alkylenedioxy groups such as methylenedioxy and ethylenedioxy), hydroxyl group, nitro group, cyano group, mercapto group, sulfo group, sulfino group, phosphono group, sulfamoyl group, monoalkylsulfamoyl group (e.g. mono-$C_{1-6}$ alkylsulfamoyl groups such as N-methylsulfamoyl, N-ethylsulfamoyl, N-propylsulfamoyl, N-isopropylsulfamoyl and N-butylsulfamoyl), dialkylsulfamoyl group (e.g. di-$C_{1-6}$ alkylsulfamoyl groups such as N,N-dimethylsulfamoyl, N,N-diethylsulfamoyl, N,N-dipropylsulfamoyl and N,N-dibutylsulfamoyl), alkylthio group (e.g. $C_{1-6}$ alkylthio groups such as methylthio, ethylthio, propylthio, isopropylthio, butylthio, sec-butylthio and tert-butylthio), arylthio group (e.g. $C_{6-10}$ arylthio groups such as phenylthio and naphthylthio), lower alkylsulfinyl group (e.g. $C_{1-6}$ alkylsulfinyl groups such as methylsulfinyl, ethylsulfinyl, propylsulfinyl and butylsulfinyl), arylsulfinyl group (e.g. $C_{6-10}$ arylsulfinyl groups such as phenylsulfinyl and napthylsulfinyl), lower alkylsulfonyl group (e.g. $C_{1-6}$ alkylsulfonyl groups such as methylsulfonyl, ethylsulfonyl, propylsulfonyl and butylsulfonyl), and arylsulfonyl group (e.g. $C_{6-10}$ arylsulfonyl groups such as phenylsulfonyl and napthylsulfonyl). Among others, $C_{6-10}$ aryl group and $C_{7-11}$ aralkyl group are preferable.

The "heterocyclic group" of the "optionally substituted heterocyclic group" may optionally have 1 to 5, preferably 1 to 3 of the above-mentioned substituents at any possible position, and, when the number of the substituent is two or more, each substituent may be the same as or different from one another.

"Optionally substituted amino group" represented by $R^3$ includes, for example, an amino group which may optionally have, as substituents, one or two of the above-mentioned "optionally substituted hydrocarbon groups" for example. Preferable examples of the substituents which the "amino group" may optionally have include lower alkyl groups (e.g. $C_{1-6}$ alkyl groups such as methyl, ethyl and propyl), lower alkenyl groups ($C_{2-6}$ alkenyl groups such as 2-propenyl and 2-butenyl), lower alkynyl groups (e.g. $C_{2-6}$ alkynyl groups such as ethynyl and propargyl) and cycloalkyl groups (e.g. $C_{3-6}$ cycloalkyl groups such as cyclopropyl, cyclobutyl, cyclopentyl and cyclohexyl). The above-mentioned lower alkyl group, lower alkenyl group, lower alkynyl group and cycloalkyl may be optionally substituted by 1 to 5, preferably 1 to 3 substituents which the above-mentioned "hydrocarbon group" may optionally have.

"Substituted hydroxyl group" represented by $R^3$, means the hydroxyl group having, in place of the hydrogen atom of hydroxyl group, for example, one "optionally substituted hydrocarbon group" described above. Among them, hydroxyl group having, for example, one optionally substituted lower alkyl group, are preferable. Examples of the "lower alkyl group" include, for example, $C_{1-6}$ alkyl groups such as methyl, ethyl, propyl, isopropyl, butyl and isobutyl. The substituents which the "lower alkyl group" may optionally have are, for example, the same substituents which the above-mentioned "hydrocarbon groups" may optionally have, in the same number.

Examples of the substituent which the "substituted benzene ring" represented by ring A has and the substituent which the "optionally substituted benzene ring" represented by ring $A^a$ may optionally have, include respectively, for example, halogen atoms (e.g. fluorine, chlorine, bromine and iodine), hydroxyl group, optionally substituted hydrocarbon groups, optionally substituted amino groups, optionally substituted mercapto groups, substituted hydroxyl groups (preferably an optionally substituted lower alkoxy group), amido group (e.g. formamido, $C_{1-6}$ alkylcarbonylamino groups such as acetamido, preferably $C_{1-6}$ alkyl-carbonylamino groups), and lower alkylenedioxy groups (e.g. $C_{1-3}$ alkylenedioxy groups such as methylenedioxy and ethylenedioxy). When the substituent is a lower alkylenedioxy group, it is desirable to form a ring together with the adjacent two carbon atoms.

"Optionally substituted hydrocarbon group" includes the same groups as the above-mentioned "optionally substituted hydrocarbon groups" represented by $R^1$, $R^2$, $R^3$, $R^4$ or $R^{1a}$.

"Optionally substituted amino group" includes the same groups as the above-mentioned "optionally substituted amino group" represented by $R^3$.

"Optionally substituted mercapto group" means a mercapto group optionally having, in place of the hydrogen atom of the mercapto group, for example, one "optionally substituted hydrocarbon group" represented by $R^1$, $R^2$, $R^3$, $R^4$ or $R^{1a}$. Preferable substituents, which the "optionally substituted mercapto group" may optionally have, include, for example, alkyl group (e.g. $C_{1-6}$ alkyl groups such as methyl, ethyl, propyl, isopropyl, butyl, isobutyl, sec-butyl, tert-butyl, pentyl and hexyl), aryl group (e.g. $C_{6-14}$ aryl groups such as phenyl, 1-naphthyl, 2-naphthyl, biphenyl, 2-indenyl and 2-anthryl) and heterocyclic groups. Among them, $C_{1-6}$ alkyl groups are preferable. The "heterocyclic groups" include the same groups as the above-mentioned "heterocyclic groups" represented by $R^2$.

The "substituted hydroxyl groups" include, for example, the same groups as the "substituted hydroxyl groups" represented by $R^3$.

The "lower alkoxy group" of "optionally substituted lower alkoxy group" include, for example, $C_{1-6}$ alkoxy groups such as methoxy, ethoxy, propoxy, isopropoxy, butoxy, isobutoxy, pentyloxy and hexyloxy. Examples of the substituents which the "lower alkoxy group" may optionally have include, for example, the same groups as the substituents which the above-mentioned "hydrocarbon group" may optionally have, preferably, for example, aryl groups, in substantially the same number.

The above-mentioned "substituted benzene ring" has 1 to 3 of the above-mentioned substituents on the benzene ring at any possible position, and, when the number of the substituents is two or more, the respective substituents may be the same as or different from one another.

The above-mentioned "optionally substituted benzene ring" may optionally have 1 to 3 of, for example, the above-mentioned substituents at any possible position on the benzene ring, and, when the number of the substituents is two or more, the respective substituents may be the same as or different from one another.

Preferable examples of the above-mentioned "substituted benzene ring" and "optionally substituted benzene ring" include benzene rings substituted by 1 to 3 substituents selected from the group consisting of halogen atoms (e.g. fluorine, chlorine, bromine and iodine), $C_{1-6}$ alkyl groups (e.g. methyl and ethyl) and $C_{1-6}$ alkoxy groups (e.g. methoxy, ethoxy, propoxy, isopropoxy, butoxy, isobutoxy, pentyloxy and hexyloxy).

Among others, benzene rings substituted by 1 or 2 substituents selected from the group consisting of halogen atoms and $C_{1-6}$ alkoxy groups are more preferable. Especially, benzene rings substituted by one of, for example, $C_{1-3}$ alkoxy groups (e.g. methoxy) are preferable.

The "$C_{2-4}$ alkylene group" of the "optionally substituted $C_{2-4}$ alkylene group" represented by X means a divalent group formed by removing two hydrogen atoms from a $C_{2-4}$ alkane. Examples of the "$C_{2-4}$ alkylene group" include, for example, ethylene, propylene, trimethylene and tetramethylene. Among these, a straight-chain $C_{2-4}$ alkylene group is preferable. Especially, ethylene group is preferable.

Examples of the substituents, which the "$C_{2-4}$ alkylene group" of the "optionally substituted $C_{2-4}$ alkylene group" represented by X may optionally have, include, for example, optionally substituted hydrocarbon groups, halogen atoms (e.g. fluorine, chlorine, bromine and iodine), nitro group, cyano group, hydroxyl group, lower alkoxy groups (e.g. $C_{1-6}$ alkoxy groups such as methoxy, ethoxy, propoxy, isopropoxy, butoxy, isobutoxy, pentyloxy and hexyloxy), amino group, mono-lower alkylamino groups (e.g. mono-$C_{1-6}$ alkylamino groups such as methylamino and ethylamino), di-lower alkylamino groups (e.g. di-$C_{1-6}$ alkylamino groups such as dimethylamino and dimethylamino), lower alkylcarbonyl groups (e.g. $C_{1-6}$ alkyl-carbonyl groups such as acetyl and propionyl), and $C_{6-10}$ aryloxy groups (e.g. phenyloxy and naphthyloxy). Among others, optionally substituted hydrocarbon groups are preferred.

The "optionally substituted hydrocarbon groups" include the same groups as the above-mentioned "optionally substituted hydrocarbon groups" represented by $R^1$, $R^2$, $R^3$, $R^4$ or $R^{1a}$.

The "$C_{2-4}$ alkylene group" of the "optionally substituted $C_{2-4}$ alkylene group" may optionally have 1 to 3, preferably 1 to 2, of, for example, the above mentioned substituents at any possible position on the $C_{2-4}$ alkylene group, and, when the number of the substituent is two or more, the respective substituents may be the same as or different from one another.

"Lower alkylene group" of the "optionally substituted lower alkylene group" represented by Y or $X^a$ means a divalent group formed by removing two hydrogen atoms from $C_{1-6}$ alkane. The "lower alkylene group" include, for example, $C_{1-6}$ alkylene groups such as methylene, ethylene, propylene, trimethylene, tetramethylene, pentamethylene, butylene, isobutylene and pentylene. Among others, a straight-chain $C_{1-3}$ alkylene group is preferable.

Examples of the substituents, which the "lower alkylene group" of the "optionally substituted lower alkylene group" represented by Y or $X^a$ may optionally have, include the same substituents, which the above-mentioned "$C_{2-4}$ alkylene group" may optionally have, in substantially the same number.

"$C_{1-6}$ Alkoxy group" represented by $R^5$ include, for example, methoxy, ethoxy, propoxy, isopropoxy, butoxy, isobutoxy, pentyloxy and hexyloxy. Among others, methoxy group is preferable.

In the above-mentioned formulae, preferable examples of the "hydrocarbon groups" of the "optionally substituted hydrocarbon groups" represented by $R^1$ or $R^{1a}$ include alkyl groups (e.g. $C_{1-6}$ alkyl groups such as methyl, ethyl, propyl and isopropyl), alkenyl groups (e.g. $C_{2-6}$ alkenyl groups such as vinyl and allyl), alkynyl groups (e.g. $C_{2-6}$ alkynyl groups such as ethynyl and propargyl) and cycloalkyl groups (e.g. $C_{3-6}$ cycloalkyl groups such as cyclopropyl, cyclobutyl, cyclopentyl and cyclohexyl). Among them, lower alkyl groups (e.g. $C_{1-6}$ alkyl groups such as methyl) and lower cycloalkyl groups (e.g $C_{3-6}$ cyclopropyl such as cyclopropyl) are further preferable. The "alkyl groups", "alkenyl groups", "alkynyl groups" and "cycloalkyl groups" may optionally have, for example, 1 to 5, preferably 1 to 3, substituents (preferably e.g. halogen atoms), which the above-mentioned "hydrocarbon groups" may optionally have.

Preferable examples of $R^1$ or $R^{1a}$ include hydrogen atom and a lower alkyl group. Among others, hydrogen is more preferable.

Preferable examples of the "hydrocarbon groups" of the "optionally substituted hydrocarbon groups" represented by $R^2$ include aryl groups (e.g. $C_{6-14}$ aryl groups such as phenyl, 1-naphthyl, 2-naphthyl, biphenyl, 2-indenyl and 2-anthryl), alkyl groups (e.g. $C_{1-6}$ alkyl groups such as methyl, ethyl, propyl and isopropyl), alkenyl groups (e.g. $C_{2-6}$ alkenyl groups such as vinyl and allyl), alkynyl groups (e.g. $C_{2-6}$ alkynyl groups such as ethynyl and propargyl), and cycloalkyl groups (e.g. $C_{3-6}$ cycloalkyl groups such as cyclopropyl, cyclobutyl, cyclopentyl and cyclohexyl). Among others, $C_{6-14}$ aryl groups, lower alkyl groups (e.g. $C_{1-6}$ alkyl groups such as methyl) and lower cycloalkyl groups (e.g. $C_{3-6}$ cycloalkyl such as cyclopropyl) are preferable and $C_{6-14}$ aryl groups are further preferable. The "aryl groups", "alkyl groups", "alkenyl groups", "alkynyl groups" and "cycloalkyl groups" may optionally have, for example, 1 to 5, preferably 1 to 3, substituents (preferably e.g. halogen atoms), which the above-mentioned "hydrocarbon groups" may optionally have.

Preferable examples of the "heterocyclic groups" of the "optionally substituted heterocyclic groups" represented by $R^2$ include 5- or 6-membered heteroaromatic groups optionally condensing with one benzene ring (preferably monocyclic heteroaromatic groups) such as 2-, 3- or 4-pyridyl, 2- or 3-thienyl, 2- or 3-furyl, 2-, 4- or 5-imidazolyl, and 2- or 3-indolyl. These heterocyclic groups may optionally have 1 to 5, preferably 1 to 3, substituents (preferably e.g. halogen atoms), which the above-mentioned "heterocyclic groups" may optionally have.

Preferable examples of $R^2$ include (i) hydrogen atom, (ii) a $C_{6-14}$ aryl (e.g. phenyl, 1-naphthyl, 2-naphthyl, biphenyl, 2-indenyl and 2-anthryl) or 5- or 6-membered heteroaromatic group (e.g. 2-, 3- or 4-pyridyl, 2-, 4- or 5-imidazolyl and 2- or 3-thienyl), each of which groups may be substituted by 1 to 5 substituents selected from the group consisting of halogen atoms, $C_{1-6}$ alkoxy, $C_{1-6}$ alkyl and $C_{6-10}$ aryl and (iii) lower alkyl groups (e.g. $C_{1-6}$ alkyl groups such as methyl, ethyl, propyl and butyl). More preferred hydrogen and phenyl group. Especially preferred is phenyl group.

Preferable examples of the "hydrocarbon groups" of the "optionally substituted hydrocarbon groups" represented by $R^3$ include alkyl groups (e.g. $C_{1-6}$ alkyl groups such as methyl, ethyl, propyl and isopropyl), alkenyl groups (e.g. $C_{2-6}$ alkenyl groups such as vinyl and allyl), alkynyl groups (e.g. $C_{2-6}$ alkynyl groups such as ethynyl and propargyl), and cycloalkyl groups (e.g. $C_{3-6}$ cycloalkyl groups such as cyclopropyl, cyclobutyl, cyclopentyl and cyclohexyl). Among these, lower alkyl groups (e.g. $C_{1-6}$ alkyl groups such as methyl), lower cycloalkyl groups (e.g. $C_{3-6}$ cycloalkyl groups such as cyclopropyl) are further preferable. The said "alkyl groups", "alkenyl groups", "alkynyl groups" and "cycloalkyl groups" may optionally have, for example, 1 to 5, preferably 1 to 3, substituents (preferably e.g. halogen atoms), which the above-mentioned "hydrocarbon groups" may optionally have.

Preferable substituents of the "optionally substituted amino group" represented by $R^3$ are one or two of, for example, (i) an optionally substituted lower alkyl group and (ii) an optionally substituted aryl group. The "lower alkyl group" includes, for example, $C_{1-6}$ alkyl groups such as methyl, ethyl, propyl, isopropyl, butyl, isobutyl, sec-butyl and tert-butyl. The "lower alkyl group" may optionally have, for example, 1 to 3 substituents which the above-mentioned "hydrocarbon group" may optionally have. The "aryl group" are, for example, $C_{6-10}$ aryl groups such as phenyl group. The "aryl group" may optionally have, for example, 1 to 5, preferably 1 to 3, substituents which the above-mentioned "hydrocarbon groups" may optionally have, (preferably halogen atoms such as fluorine and chlorine, or $C_{1-6}$ alkoxy groups such as methoxy and ethoxy). The "optionally substituted amino groups" represented by $R^3$ are, for example, a phenylamino group substituted with 1 to 3 lower alkoxy groups (e.g. methoxy).

Preferable substituents of the "substituted hydroxyl group" represented by $R^3$ include, for example, optionally substituted lower alkyl groups (e.g. $C_{1-6}$ alkyl groups such as methyl, ethyl, propyl, isopropyl, butyl, sec-butyl and tert-butyl). The "lower alkyl group" may optionally have, for example, 1 to 3 substituents which the above-mentioned "hydrocarbon group" may optionally have. Preferable ones of the "substituted hydroxyl groups" represented by R include, for example, a lower alkoxy group which may have 1 to 3 substituents, (e.g. $C_{1-6}$ alkoxy groups such as methoxy, ethoxy, propoxy, isopropoxy and butoxy). The substituents of the "lower alkoxy group" are, for example, substituents which the above-mentioned "hydrocarbon group" may optionally have.

$R^3$ is preferably optionally substituted hydrocarbon groups. Among others, i) optionally substituted lower alkyl groups and ii) optionally substituted lower cycloalkyl groups are preferable and optionally substituted lower alkyl groups are more preferable. Preferable examples of the "lower alkyl groups" include $C_{1-6}$ alkyl groups such as methyl, ethyl, propyl and isopropyl. Preferable examples of the "lower cycloalkyl groups" include $C_{3-6}$ cycloalkyl groups such as cyclopropyl, cyclobutyl, cyclopentyl and cyclohexyl. The "lower alkyl groups" and "lower cycloalkyl groups" may optionally have, for example, 1 to 3 substituents which the above-mentioned "hydrocarbon groups" may optionally have, respectively. Preferable examples of $R^3$ include optionally halogenated $C_{1-6}$ alkyl groups (e.g. methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl) and $C_{3-6}$ cycloalkyl groups (e.g. cyclopropyl, cyclobutyl, cyclopentyl and cyclohexyl). More preferable example is an optionally halogenated $C_{1-6}$ alkyl group.

$R^4$ is preferably hydrogen atom or optionally substituted lower alkyl groups (e.g. $C_{1-6}$ alkyl groups such as methyl, ethyl, propyl, isopropyl, butyl, isobutyl, sec-butyl and tert-butyl). The "lower alkyl groups" may optionally have, for example, 1 to 5, preferably 1 to 3, substituents (preferably e.g. halogen atoms), which the above-mentioned "hydrocarbon groups" may optionally have. $R^1$ is, more preferably, hydrogen atom or $C_{1-4}$ alkyl groups (e.g. methyl). Especially hydrogen atom is preferable.

The ring A and ring $A^a$ are preferably benzene rings substituted by 1 or 2 substituents selected from the group consisting of lower alkoxy group (e.g. $C_{1-6}$ alkoxy groups such as methoxy and ethoxy) and halogen atom (e.g. fluorine, chlorine, bromine and iodine). Among others, the ring of the formula:

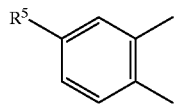

wherein $R^5$ represents a $C_{1-6}$ alkoxy group is more preferable. $R^5$ is preferably a methoxy group.

X is preferably, for example, $C_{2-4}$ alkylene groups (e.g. ethylene, trimethylene, tetramethylene and propylene) which may optionally have one or two optionally substituted hydrocarbon groups. More preferred are straight $C_{2-3}$ alkylene groups optionally having one or two lower alkyl groups (e.g. $C_{1-6}$ alkyl groups such as methyl, ethyl, propyl, isopropyl, butyl, isobutyl, sec-butyl and tert-butyl). X is furthermore preferably ethylene group optionally substituted with one or two methyl groups. X is, especially preferably, an ethylene group.

$X^a$ is preferably, for example, lower alkylene groups (e.g. $C_{1-6}$ alkylene groups such as methylene, ethylene, trimethylene, tetramethylene, propylene, butylene, isobutylene and pentylene) which may optionally have one or two optionally substituted hydrocarbon groups. More preferred are straight-chain $C_{2-3}$ alkylene groups (e.g. ethylene and trimethylene) optionally having one or two lower alkyl groups (e.g. $C_{1-6}$ alkyl groups such as methyl, ethyl, propyl, isopropyl, butyl, isobutyl, sec-butyl and tert-butyl). $X^a$ is furthermore preferably ethylene group optionally substituted with one or two methyl groups. $X^a$ is, especially preferably, an ethylene group.

Y is preferably, for example, i) a bond or ii) methylene groups optionally having one or two substituents selected from halogen atoms and optionally substituted hydrocarbon groups. Y is more preferably a bond or a methylene group. Especially, a bond is preferable.

......... is preferably a single bond.

Preferable examples of the compounds (I) of this invention or salts thereof include the compounds wherein $R^1$ is hydrogen, $R^2$ is (i) hydrogen or (ii) an aryl group (e.g. $C_{6-14}$ aryl groups such as phenyl, 1-naphthyl, 2-naphthyl, biphenylyl, 2-indenyl and 2-anthryl) or a 5- or 6-membered heteroaromatic group (e.g. 2-, 3- or 4-pyridyl, 2-, 4- or 5-imidazolyl and 2- or 3-thienyl), each of which groups may be substituted by 1 to 5, preferably 1 to 3, substituents selected from the group consisting of halogen, $C_{1-6}$ alkoxy, $C_{1-6}$ alkyl and $C_{6-10}$ aryl, $R^3$ is optionally halogenated $C_{1-6}$ alkyl groups (e.g. methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, and 6,6,6-trifluorohexyl), or $C_{3-6}$ cycloalkyl groups (e.g. cyclopropyl, cyclobutyl, cyclopentyl and cyclohexyl), $R^4$ is hydrogen, ring A is a benzene ring substituted with a lower alkoxy group (e.g. $C_{1-6}$ alkoxy groups such as methoxy and ethoxy) or a halogen atom (e.g. fluorine, chlorine, bromine and iodine), X is a $C_{2-4}$ alkylene group (e.g. ethylene, trimethylene and propylene, preferably ethylene group), and Y is a bond or a methylene group optionally substituted with a halogen atom (e.g. fluorine, chlorine, bromine and iodine), preferably a bond or a methylene group.

Furthermore preferred is the compound wherein $R^1$ is hydrogen, $R^2$ is hydrogen, a $C_{6-10}$ aryl group or a $C_{6-10}$ aryl-$C_{1-4}$ alkyl group (e.g. benzyl and phenethyl), $R^3$ is a $C_{1-6}$ alkyl group which may be substituted by 1 to 3 halogens, $R^4$ is hydrogen, ring A is a benzene ring substituted by 1 or 2 substituents selected from the group consisting of halogen and a $C_{1-6}$ alkoxy group, X is a C$_{2-4}$ alkylene group, and Y is a bond or a methylene group.

More preferable compounds are exemplified by those wherein

R$^1$ is hydrogen,

R$^2$ is hydrogen or a phenyl group,

R$^3$ is an optionally halogenated C$_{1-3}$ alkyl group (e.g. methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl and isopropyl), R$^4$ is hydrogen, ring A is

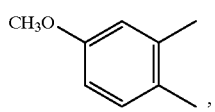

X is an ethylene group, and

Y is a bond.

Preferable examples of the compounds (I$^a$) or salts thereof include compounds wherein R$^{1a}$ is hydrogen, R$^2$ is (i) hydrogen or (ii) an aryl group (e.g. C$_{6-14}$ aryl groups such as phenyl, 1-naphthyl, 2-naphthyl, biphenylyl, 2-indenyl and 2-anthryl) or a 5- or 6-membered heteroaromatic group, each of which groups may be substituted by 1 to 5, preferably 1 to 3, substituents selected from the group consisting of halogen, C$_{1-6}$ alkoxy, C$_{1-6}$ alkyl and C$_{6-10}$ aryl, R$^3$ is an optionally halogenated C$_{1-6}$ alkyl group (e.g. methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl) or a C$_{3-6}$ cycloalkyl group (e.g. cyclopropyl, cyclobutyl, cyclopentyl and cyclohexyl).

R$^4$ is hydrogen, ring A$^a$ is a benzene ring substituted with a lower alkoxy group (e.g. C$_{1-6}$ alkoxy groups such as methoxy and ethoxy) or a halogen atom (e.g. fluorine, chlorine, bromine and iodine), X$^a$ is a C$_{2-4}$ alkylene group (e.g. ethylene, trimethylene and propylene), Y is a bond or a methylene group optionally having a halogen atom (e.g. fluorine, chlorine, bromine and iodine), and ╌╌╌ is a single bond.

More preferable compounds are exemplified by those wherein

R$^{1a}$ is hydrogen,

R$^2$ is hydrogen or a phenyl group,

R$^3$ is an optionally substituted C$_{1-3}$ alkyl group (e.g. methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl and isopropyl), R$^4$ is hydrogen, ring A$^a$ is

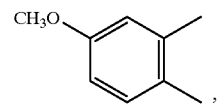

X$^a$ is an ethylene group,

Y is a bond, and

╌╌╌ is a single bond.

Specific examples of the compound (I) of this invention or the compound (I$^a$) include 2,2,2-trifluoro-N-[2-(5-methoxy-2-phenyl-1H-inden-3-yl)ethyl]acetamide, 2,2,2-trifluoro-N-[2-(5-methoxy-1H-inden-3-yl)ethyl]acetamide, 2,2,2-trifluoro-N-[2-(7-methoxy-3,4-dihydronaphthalen-1-yl)ethyl]acetamide, N-[2-(7-methoxy-3,4-dihydronaphthalen-1-yl)ethyl]acetamide, N-[2-(5-methoxy-1H-inden-3-yl)ethyl]propionamide and N-[2-(5-methoxy-1H-inden-3-yl)ethyl]butyramide. Among others, preferred are 2,2,2-trifluoro-N-[2-(5-methoxy-2-phenyl-1H-inden-3-yl)ethyl]acetamide, N-[2-(5-methoxy-1H-inden-3-yl)ethyl]propionamide and N-[2-(5-methoxy-1H-inden-3-yl)ethyl]butyramide.

Examples of the salts of the compounds (I) or (I$^a$) include, for example, the salts employed as intermediates for the synthesis and salts which are pharmaceutically employable. For example, salts with inorganic bases, salts with organic bases, salts with inorganic acids, salts with organic acids, and salts with basic or acidic amino acid. Preferable examples of the salts with inorganic bases include alkali metal salts such as sodium salt and potassium salt, alkaline earth metal salts such as calcium salt and magnesium salt, aluminum salt and ammonium salt. Preferable examples of the salts with organic bases include salts with, for example, trimethylamine, triethylamine, pyridine, picoline, 2,6-lutidine, ethanolamine, diethanolamine, triethanolamine, cyclohexylamine, dicyclohexylamine and N,N'-dibenzyl ethylenediamine. Preferable examples of the salts with inorganic acids include salts with hydrochloric acid, hydrobromic acid, nitric acid, sulfuric acid and phosphoric acid. Preferable examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid and p-toluenesulfonic acid. As preferable examples of the salts with basic amino acids, mention is made of salts with, for example, arginine, lysine and ornithine. As preferable examples of the salts with acidic amino acid, mention is made of salts with, for example, aspartic acid and glutamic acid.

Among them, pharmaceutically acceptable salts are preferable, which are exemplified by, when the compound (I) contains a basic functional group, salts with an inorganic acid such as hydrochloric acid, hydrobromic acid, nitric acid, sulfuric acid or phosphoric acid, and, salts with an organic acid such as acetic acid, phthalic acid, fumaric acid, tartaric acid, maleic acid, citric acid, succinic acid, methanesulfonic acid or p-toluenesulfonic acid, and, when the compound (I) contains an acid functional group, for example, alkali metal salts such as sodium salt and potassium salt, alkaline earth metal salts such as calcium salt and magnesium salt, and ammonium salt.

The following is the description on the method of producing the compound (I) and the compound (I$^a$) or salts thereof [hereinafter simply referred to as the compound (I$^a$)].

The compound (I) of this invention can be produced by, for example, the methods shown by the following reaction schemes or those analogous thereto. And, the compound (I") can be produced by, for example, the methods shown by the following reaction schemes, methods analogous thereto or the methods described on the above-mentioned references, Tetrahedron Letters, p.2085 (1969), Journal of Chemical Society (C) p.3506 (1971), U.S. Pat. No. 5,158,948, U.S. Pat. No. 3,642,785, and JP-A-60-142932.

In the following reaction schemes, symbols used in the respective compounds are of the same meaning as defined above.

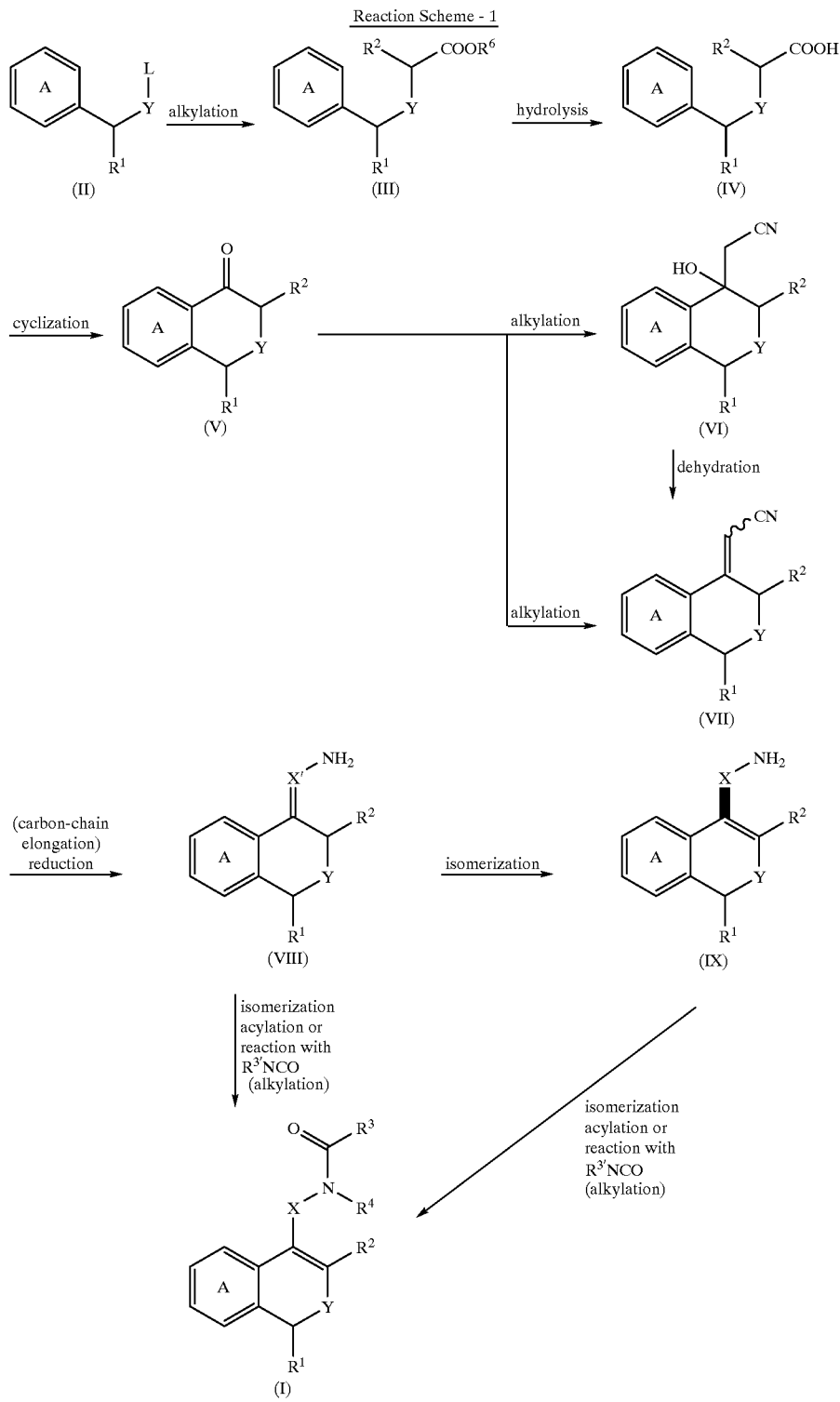

Reaction Scheme - 2

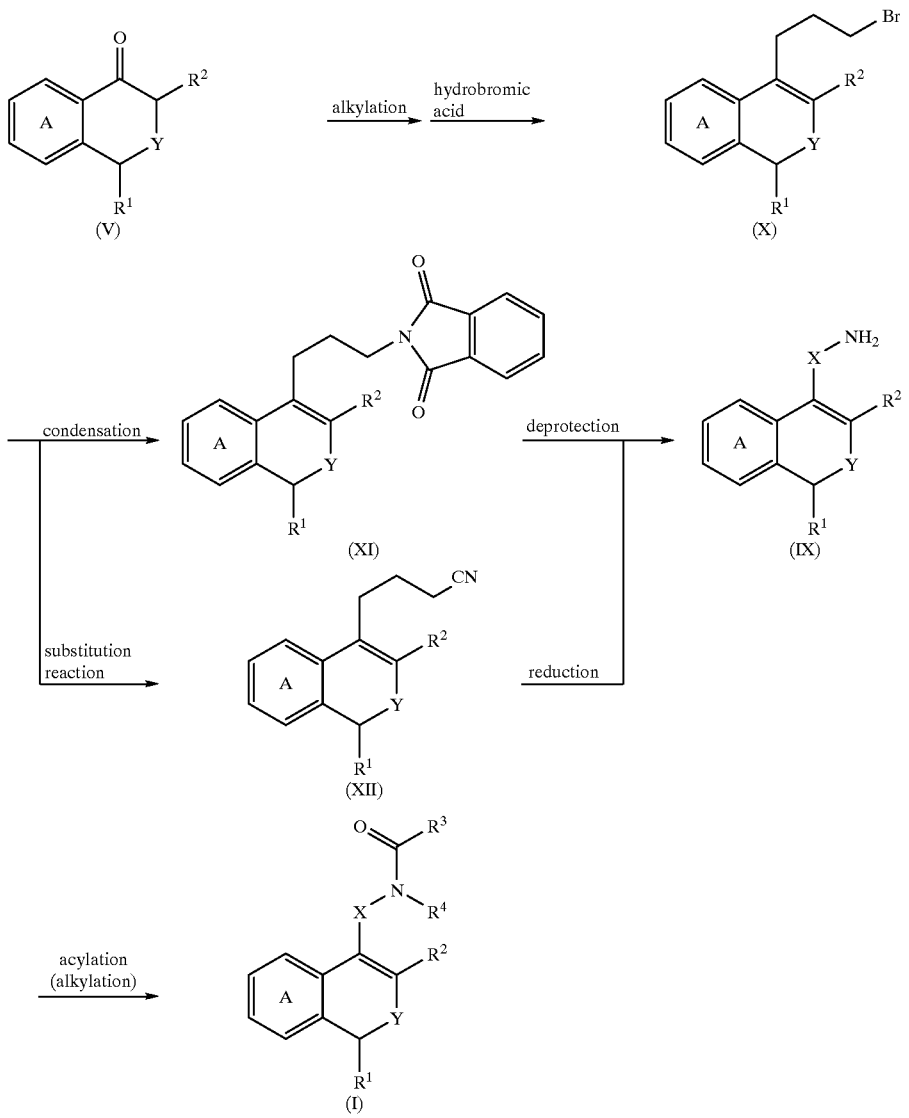

The compounds (II) to (XII) in the formulae includes the corresponding salts. As such salts, use is made of, for example, substantially the same salts as those of the compound (I).

The compound (II) wherein L represents a halogen atom, an alkyl sulfonyl group, an alkylsulfonyloxy group or an arylsulfonyloxy group can be produced by per se known methods, for example, methods described in J. Org. Chem., Vol.54, p.491 (1989), Vol.57, p.3772 (1992), and Bull. Chem. Soc. Jpn., Vol.55, p.918 (1982), or methods analogous thereto.

Examples of the halogen atom represented by L include, for example, fluorine, chlorine, bromine and iodine. Examples of the alkylsulfonyl group represented by L include, for example, $C_{1-5}$ alkylsulfonyl groups (e.g. methanesulfonyl and ethanesulfonyl). Examples of the alkylsulfonyloxy group represented by L include, for example, optionally halogenated $C_{1-5}$ alkylsulfonyloxy groups (e.g. methanesulfonyloxy, ethanesulfonyloxy and trichloromethanesulfonyloxy). Examples of the arylsulfonyloxy group represented by L include, for example, optionally substituted benzenesulfonyloxy groups (e.g. p-toluenesulfonyloxy and benzenesulfonyloxy).

The compound (V) can be produced by per se known methods, for example, methods described on J. Org. Chem. Vol.55, p.1874 (1990), J. Am. Chem. Soc. Vol.105, p.3992 (1983), J. Chem. Soc., Perkin. Trans. I, p.3399 (1988), Liebigs. Ann. Chem. p.263 (1987), Organometallics Vol.10, p.508 (1991), J. Med. Chem. Vol.8, p.53 (1965), and U.S. Pat. No. 5,059,609, or methods analogous thereto as well.

And, when the compounds in the formulae are commercially available ones, the compounds on the market can be used as they are, when so desired.

The compound (III) [wherein $R^6$ represents a hydrocarbon group] can be produced by allowing the compound (II) to react with an ester derivative represented by the formula: $R^2CH_2COOR^6$ [wherein $R^2$ and $R^6$ are as defined above] in the presence of a base. The "hydrocarbon group" represented by $R^6$ includes, for example, the above-mentioned "hydrocarbon group", and, among others, lower alkyl groups (e.g. $C_{1-6}$ alkyl such as methyl, ethyl and isopropyl) or optionally substituted benzyl groups are preferable. The "optionally substituted benzyl group" may optionally have 1 to 3 substituents, for example, halogen atoms or $C_{1-3}$ alkyl, at any possible position on the benzyl group, specifically exemplified by benzyl, p-chlorobenzyl and p-methylbenzyl.

The ester derivative is used in an amount of about 1.0 to 5.0 mol, preferably about 1.0 to 2.0 mol, relative to 1 mol of the compound (II). Examples of the base include inorganic bases such as sodium carbonate, potassium carbonate and sodium hydrogencarbonate, aromatic amines such as pyridine and lutidine, tertiary amines such as triethylamine, tripropylamine, tributylamine, cyclohexyldimethylamine, 4-dimethylaminopyridine, N,N-dimethylaniline, N-methylpiperidine, N-methylpyrrolidine and N-methylmorpholine, alkali metal hydrides such as sodium hydride and potassium hydride, metal amides such as sodium amide, lithium diisopropyl amide and lithium hexamethyl disilazide, and metal alkoxides such as sodium methoxide, sodium ethoxide and potassium tertiary butoxide. These bases are used, relative to 1 mol of the compound (II), in an amount of about 1.0 to 5.0 mol, preferably about 1.0 to 2.0 mol. Use of a solvent inert to the reaction is advantageous for conducting this reaction. While, as the solvent, any one can be used so long as it does not hamper the proceeding of the reaction, for example, alcohols such as methanol, ethanol and propanol, ethers such as diethyl ether, tetrahydrofuran, dioxane and 1,2-dimethoxyethane, hydrocarbons such as benzene, toluene, cyclohexane and hexane, amides such as N,N-dimethylformamide and N,N-dimethylacetamide, halogenated hydrocarbons such as dichloromethane, chloroform, carbon tetrachloride and 1,2-dichloroethane, nitrites such as acetonitrile and propionitrile, ketones such as acetone and methyl ethyl ketone and sulfoxide such as dimethylsulfoxide, or a suitable mixture of these solvents are preferable. The reaction time ranges usually from 30 minutes to 48 hours, preferably from 30 minutes to 5 hours. The reaction temperature ranges usually from –20 to 200° C., preferable from –10 to 150° C. While the product (III) can be optionally used for the subsequent reaction in the state of its reaction mixture or as the crude product, it can optionally be isolated from the reaction mixture by a conventional procedure, and can be readily purified by means of, for example, recrystallization, distillation and chromatography.

The compound (IV) can be produced by subjecting the ester group of the compound (III) to hydrolysis using an acid or a base. The acid hydrolysis is conducted by using, for example, a mineral acid such as hydrochloric acid and sulfuric acid, a Lewis acid such as boron trichloride and boron tribromide, a combination of a Lewis acid and a thiol or a sulfide, and an organic acid such as trifluoroacetic acid and p-toluenesulfonic acid. The alkali hydrolysis is conducted by using, for example, a metal hydroxide such as sodium hydroxide, potassium hydroxide or barium hydroxide, a metal carbonate such as sodium carbonate and potassium carbonate, a metal alkoxide such as sodium methoxide, sodium ethoxide and potassium tert.-butoxide, and an organic base such as triethylamine, imidazole and formamidine. The above acid or base is used in an amount of about 0.5 to 10 mol, preferably about 0.5 to 3.0 mol, relative to 1 mol of the compound (III). This reaction is advantageously conducted in the absence of solvent or in the presence of a solvent inert to the reaction. While, as the solvent, any one can be used so long as it does not hamper the proceeding of the reaction, for example, alcohols such as methanol, ethanol and propanol, aromatic hydrocarbons such as benzene and toluene, saturated hydrocarbons such as cyclohexane and hexane, organic acids such as formic acid and acetic acid, ethers such as tetrahydrofuran, dioxane and 1,2-dimethoxyethane, amides such as N,N-dimethylformamide and N,N-dimethylacetamide, halogenated hydrocarbons such as dichloromethane, chloroform, carbon tetrachloride and 1,2-dichloroethane, nitrites such as acetonitrile and propionitrile, ketones such as acetone and methyl ethyl ketone and sulfoxide such as dimethyl sulfoxide, water or a suitable mixture of these solvents are preferable. The reaction time ranges usually from 10 minutes to 60 hours, preferably from 10 minutes to 12 hours. The reaction temperature ranges usually from –10 to 200° C., preferable from 0 to 120° C. While the product (IV) can be optionally used for the subsequent reaction in the state of its reaction mixture or as the crude product, it can optionally be isolated from the reaction mixture by a conventional procedure, and can be readily purified by means of, for example, recrystallization, distillation and chromatography.

The compound (V) is produced by subjecting the compound (IV) to cyclization. The cyclization is conducted by per se known method, for example, a method by heating, a method using an acid substance, a method comprising the reaction with a halogenating agent and then conducting cyclization in the presence of a Lewis acid, and methods analogous thereto.

The cyclization under heating is advantageously conducted in the absence of solvent or in the presence of a solvent inert to the reaction. While, as the solvent, any one can be used so long as it does not hamper the proceeding of the reaction, for example, hydrocarbons having a high boiling point such as 1,2,3,4-tetrahydronaphthalene, ethers having a high boiling point such as diphenyl ether and diethylene glycol dimethyl ether, and a suitable mixture solvent of them are preferable. The reaction time ranges usually from 10 minutes to 24 hours, preferably from 10 minutes to 10 hours. The reaction temperature ranges usually from 100 to 300° C., preferably from 100 to 200° C.

When the cyclization is conducted by using an acid substance, the acid substance includes, for example, phosphorus oxychloride, phosphorus pentachloride, phosphorus trichloride, thionyl chloride, hydrochloric acid, sulfuric acid and polyphosphoric acid. The amount of the acid substance is about 0.5 to 100 mol, preferably about 5.0 to 20 mol, relative to 1 mol of the compound (IV). It is advantageous to conduct this reaction in the absence of solvent or in the presence of a solvent inert to the reaction. While, as the solvent, any one can be employed so long as it does not hamper the proceeding of the reaction, for example, aromatic hydrocarbons such as benzene and toluene, saturated hydrocarbons such as cyclohexane and hexane, ethers such as tetrahydrofuran, dioxane and 1,2-dimethoxyethane, amides such as N,N-dimethylformamide and N,N-dimethylacetamide, halogenated hydrocarbons such as dichloromethane, chloroform, carbon tetrachloride and 1,2-dichloroethane, acid anhydrides such as acetic anhydride, sulfoxides such as dimethyl sulfoxide or a suitable mixture solvent of them are preferable. The reaction time ranges usually from 30 minutes to 12 hours, preferably from 30 minutes to 6 hours. The reaction temperature ranges usually from 0 to 200° C., preferably from 0 to 150° C.

In the case where the cyclization is conducted in the presence of a Lewis acid after the compound (IV) is allowed to react with a halogenating agent, the halogenating agent is exemplified by halogenated thionyls such as thionyl chloride and thionyl bromide, halogenated phosphoryls such as phosphoryl chloride and phosphoryl bromide, phosphorus halogenides such as phosphorus pentachloride, phosphorus trichloride, phosphorus pentabromide and phosphorus tribromide, oxalyl halides such as oxalyl chloride and phosgene. The halognating agent is used in an amount of about 1.0 to 30 mol, preferably about 1.0 to 10 mol, relative to 1 mol of the compound (IV). This reaction is advantageously conducted in the absence of solvent or in the presence of a solvent inert to the reaction. While, as the solvent, any one can be employed so long as it does not hamper the proceeding of the reaction, for example, aromatic hydrocarbons such as benzene and toluene, saturated hydrocarbons such as cyclohexane and hexane, ethers such as tetrahydrofuran, dioxane and 1,2-dimethoxyethane, amides such as N,N-dimethylformamide and N,N-dimethylacetamide, halogenated hydrocarbons such as dichloromethane, chloroform, carbon tetrachloride and 1,2-dichloroethane, or a suitable mixture solvent of them are preferable. The reaction time ranges usually from 10 minutes to 12 hours, preferably from 10 minutes to 5 hours. The reaction temperature ranges usually from −10 to 200° C., preferably from −10 to 120° C. While the product can be optionally used for the subsequent reaction in the state of its reaction mixture or as the crude product, it can optionally be isolated from the reaction mixture by a conventional procedure, and can be readily purified by means of, for example, recrystallization and distillation, which is then processed with a Lewis acid. Examples of the Lewis acid include, for example, anhydrous aluminum chloride, anhydrous zinc chloride and anhydrous iron chloride. Relative to 1 mol of the compound (IV), the Lewis acid is used in an amount of about 0.1 to 20 mol, preferably 0.2 to 5.0 mol. This reaction is advantageously conducted in the absence of solvent or in the presence of a solvent inert to the reaction. While, as the solvent, any one can be employed so long as it does not hamper the proceeding of the reaction, for example, aromatic hydrocarbons such as benzene and toluene, halogenated hydrocarbons such as monochlorobenzene, o-dichlorobenzene, 1,2,4-trichlorobenzene, dichloromethane, chloroform, carbon tetrachloride and 1,2-dichloroethane, or a suitable mixture solvent of them, are preferable. The reaction times ranges usually from 30 minutes to 12 hours, preferably from 30 minutes to 6 hours. The reaction temperature ranges usually from −10 to 200° C., preferably from −10 to 120° C. While the product (V) produced by the above-mentioned cyclization reaction can be optionally used for the subsequent reaction in the state of its reaction mixture or the crude product, it can optionally be isolated from the reaction mixture by a conventional procedure, and can be readily purified by means of, for example, recrystallization, distillation and chromatography.

The compound (VII) is produced by the following procedure, namely, carboanion formed by processing acetonitrile with a base is allowed to react with the compound (V) to give the compound (VI) which is then subjected to dehydration. The compound (VII) is obtained as single E- or Z-configurational isomer or a mixture of E- and Z-isomer. Relative to 1 mol of the compound (V), acetonitrile is used in an amount of about 1.0 to 3.0 mol, preferably about 1.0 to 1.3 mol. Examples of the base include alkali metal hydrides such as sodium hydride and potassium hydride, metal amides such as sodium amide, lithium diisopropylamide and lithium hexamethyl disilazide, and metal alkoxides such as sodium methoxide, sodium ethoxide and potassium tertiary butoxide. These bases are used, relative to 1 mol of the compound (V), in an amount of about 1.0 to 5.0 mol, preferably about 1.0 to 1.5 mol. This reaction is preferably conducted by using a solvent inert to the reaction. While, as the solvent, any one can be used so long as it does not hamper the proceeding of the reaction, for example, alcohols such as methanol, ethanol and propanol, ethers such as diethyl ether, tetrahydrofuran, dioxane and 1,2-dimethoxyethane, hydrocarbons such as benzene, toluene, cyclohexane and hexane, amides such as N,N-dimethylformamide and N,N-dimethylacetamide, halogenated hydrocarbons such as dichloromethane, chloroform, carbon tetrachloride and 1,2-dichloroethane, or a suitable mixture of these solvents are preferable. The reaction time ranges usually from 30 minutes to 48 hours, preferably from 30 minutes to 5 hours. The reaction temperature ranges usually from −78 to 100° C., preferable from −78 to 50° C. While the product can be optionally used for the subsequent reaction in the state of its reaction mixture or as the crude product, it can optionally be isolated from the reaction mixture by a conventional procedure, and can be readily purified by means of, for example, recrystallization, distillation and chromatography.

Examples of the catalyst to be employed for the dehydration include acid catalysts such as hydrochloric acid, sulfuric acid, phosphoric acid, potassium hydrogensulfate, oxalic acid, p-toluenesulfonic acid, 10-camphor sulfonic acid and boron trifluoride ether complex, and basic catalyst acid such as sodium hydroxide and potassium hydroxide, and further, for example, a dehydrating agent such as N,N'-dicyclohexyl carbodiimide; alumina, sodium dioxide, phosphorus oxychloride, thionyl chloride and methanesulfonyl chloride may optionally be employed. This reaction is advantageously conducted in the absence of solvent or in the presence of a solvent inert to the reaction. While, as the solvent, any one can be used so long as it does not hamper the proceeding of the reaction, for example, alcohols such as methanol, ethanol and propanol, ethers such as diethyl ether, tetrahydrofuran, dioxane and 1,2-dimethoxyethane, hydrocarbons such as benzene, toluene, cyclohexane and hexane, amides such as N,N-dimethylformamide and N,N-dimethylacetamide, sulfoxides such as dimethyl sulfoxide, or a suitable mixture of these solvents are preferable. The reaction time ranges usually from 30 minutes to 24 hours, preferably from 30 minutes to 5 hours. The reaction temperature ranges usually from 0 to 200° C., preferably from 0 to 150° C.

And, the compound (VII) can also be obtained as E-isomer or Z-isomer singly or a mixture of them by allowing phosphonate carboanion produced by processing alkylsulfonic acid diester with a base to react with the compound (V). Examples of the alkylsulfonic acid diester include, for example, diethyl cyanomethyl phosphonate. The alkyl phosphonic acid diester is used, relative to 1 mol of the compound (V), in an amount of about 1.0 to 3.0 mol, preferably about 1.0 to 1.5 mol. Examples of the base include, for example, alkali metal hydrides such as sodium hydride and potassium hydride, metal amides such as sodium amide, lithium diisopropyl amide and lithium hexamethyl disilazide, and metal alkoxides such as sodium methoxide, sodium ethoxide and potassium tert.-butoxide. The amount of these bases to be employed ranges, relative to 1 mol of the compound (V), from about 1.0 to 5.0 mol, preferably about 1.0 to 1.5 mol. This reaction is advantageously conducted in the presence of a solvent inert to the reaction. While, as the solvent, any one can be used so long as it does not hamper the proceeding of the reaction, for example, alcohols such as methanol, ethanol and propanol, ethers such as diethyl ether, tetrahydrofuran, dioxane and 1,2-dimethoxyethane, hydrocarbons such as benzene, toluene, cyclohexane and hexane, amides such as N,N-dimethylformamide and N,N-dimethylacetamide, sulfoxides such as dimethyl sulfoxide, or a suitable mixture of these solvents are preferable. The reaction time ranges usually from 1 to 50 hours, preferably from 1 to 10 hours. The reaction temperature ranges usually from −78 to 200° C., preferably from 0 to 150° C. While the mixture of isomers of the compound (VII) can be used for the subsequent reaction in the state of the reaction mixture or a crude product, it can be isolated from the reaction mixture in accordance with a conventional method, and can be readily purified by means of, for example, recrystallization, distillation and chromatography.

Elongation of the carbon chain at the side chain of the compound (VII) can be conducted in accordance with a conventional carbon-chain elongation reaction, for example, a reaction comprising hydrolysis of cyano group under alkaline or acid conditions to give carboxyl group, or leading the carboxyl to ester form, which is then subjected to reduction to give an alcohol, followed by halogenation and cyanation is employed.

The compound (VIII) is produced by subjecting the compound (VII) to reduction. In the formula, X' represents a trivalent group formed by removing one hydrogen atom from the group represented by X described above. Examples of the reducing agent to be employed include, for example, metal hydrides such as aluminum hydride and diisobutyl aluminum hydride; metal hydride complex compounds such as lithium aluminum hydride and sodium borohydride; or, example of a hydrogenative catalyst includes Raney nickel and Raney cobalt. The amount of the reducing agent ranges, for example in the case of using a metal hydride, from about 1.0 to 10 mol, preferably from about 1.0 to 3.0 mol, relative to 1 mol of the compound (VII), and in the case of using a metal hydride complex compound, from about 1.0 to 10 mol, preferably from about 1.0 to 3.0 mol, relative to 1 mol of the compound (VII), and in the case of hydrogenation, a catalyst such as Raney nickel or Raney cobalt is used in a amount of about 10 to 1000 weight %, preferably about 100 to 300 weight % relative to the compound (VII). This reaction is advantageously conducted in the presence of a solvent inert to the reaction. While, as the solvent, any one can be used so long as it does not hamper the proceeding of the reaction, for example, alcohols such as methanol, ethanol and propanol, ethers such as diethyl ether, tetrahydrofuran, dioxane and 1,2-dimethoxyethane, hydrocarbons such as benzene, toluene and cyclohexane, amides such as N,N-dimethylformamide and N,N-dimethylacetamide, organic acids such as formic acid and acetic acid, or a suitable mixture of these solvents are preferable. In the case of using Raney nickel or Raney cobalt, amines such as ammonia may optionally be further added to suppress the occurrence of side reactions. While the reaction time varies with the activity and amount of the reducing agent or the catalyst, it ranges usually from 1 to 100 hours, preferably from 1 to 50 hours. The reaction temperature ranges usually from 0 to 120° C., preferably from 20 to 80° C. In the case of using a catalyst such as Raney nickel or Raney cobalt, the hydrogen pressure ranges usually from 1 to 100 kgf/cm². While the product (VIII) can be used for the subsequent reaction in the state of the reaction mixture or a crude product, it can be isolated from the reaction mixture in accordance with a conventional method, and can be readily purified by means of, for example, recrystallization, distillation and chromatography.

The compound (IX) is produced by processing the compound (VIII) with an acid to cause isomerization. Examples of the acid catalyst include inorganic acids such as hydrochloric acid, sulfuric acid, nitric acid, hydrobromic acid and phosphoric acid; organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid and 10-camphor sulfonic acid; and boron trifluoride ether complex. The amount of these acid catalysts to be employed ranges, relative to 1 mol of the compound (VIII), from about 0.01 to 10 mol, preferably from about 0.01 to 5.0 mol. This reaction is advantageously conducted in the absence of solvent or in the presence of a solvent inert to the reaction. While, as the solvent, any one can be used so long as it does not hamper the proceeding of the reaction, for example, alcohols such as methanol, ethanol and propanol, ethers such as diethyl ether, tetrahydrofuran, dioxane and 1,2-dimethoxyethane, hydrocarbons such as benzene, toluene, cyclohexane and hexane, amides such as N,N-dimethylformamide and N,N-dimethylacetamide, sulfoxides such as dimethyl sulfoxide, water, or a suitable mixture of these solvents are preferable. The reaction time ranges usually from 1 minutes to 12 hours, preferably from 1 minute to 2 hours. The reaction temperature ranges usually from −10 to 200° C., preferably from −10 to 100° C. While the product (IX) can be used for the subsequent reaction in the state of the reaction mixture or a crude product, it can be isolated from the reaction mixture in accordance with a conventional method, and can be readily purified by means of, for example, recrystallization, distillation and chromatography.

The compound (I) is produced by allowing the compound (IX) to react with carboxylic acid, a salt thereof or a reactive derivative thereof. Examples of the carboxylic acid include a compound represented by the formula: $R^3$—COOH [wherein $R^3$ is as defined above]. Examples of the reaction derivatives of the carboxylic acid include acid halogenides (e.g. acid chloride and acid bromide), acid amides (e.g. acid amides with pyrazole, imidazole and benzotriazole), acid anhydrides (e.g. $C_{1-6}$ aliphatic acid anhydrides such as acetic anhydride, propionic anhydride and butyric anhydride), acid azide, active esters (e.g. diethoxyphosphoric acid ester, diphenoxyphosphoric acid ester, p-nitrophenyl ester, 2,4-dinitrophenyl ester, cyanomethyl ester, pentachlorophenyl ester, ester with N-hydroxysuccinimide, ester with 1-hydroxybenzotriazole, ester with 6-chloro-1-hydroxybenzotriazole, and ester with 1-hydroxy-1H-2-pyridone), and active thioester (e.g. 2-pyridyl thioester and 2-benzothiazolyl thioester). Or, instead of using the reactive derivative, the carboxylic acid or a salt thereof may optionally be allowed to directly react with the compound (IX) in the presence of an adequate condensing agent. Examples of the condensing agent include N,N'-disubstituted carbodiimides such as N,N'-dicyclohexylcarbodiimide and 1-ethyl-3-(3-dimethylaminopropyl) carbodiimide hydrochloride (WSC), azolides such as N,N'-carbonyldiimidazole, dehydrating agents such as N-ethoxycarbonyl-2-ethoxy-1,2-dihydroquinoline, phosphorus oxychloride and alkoxy acetylene, and 2-halogenopyridinium salts such as 2-chloromethyl pyridinium iodide and 2-fluoro-1-methyl pyridinium iodide. In the case where these condensing agents are employed, the reaction is considered to proceed via a reaction derivative of carboxylic acid. The carboxylic acid represented by the formula: $R^3$—COOH ($R^3$ is as defined above) or a reactive derivative thereof is used usually in an amount of about 1.0 to 5.0 mol, preferably about 1.0 to 2.0 mol, relative to 1 mol of the compound (IX). This reaction is conducted advantageously by using a solvent inert to the reaction. While any solvent can be employed so long as it does not hamper the proceeding of the reaction, for example, ethers such as diethyl ether, tetrahydrofuran, dioxane and 1,2-dimethoxyethane, hydrocarbons such as benzene, toluene and cyclohexane, amides such as N,N-dimethylformamide and N,N-dimethylacetamide, halogenated hydrocarbons such as dichloromethane, chloroform, carbon tetrachloride and 1,2-dichloroethane, nitrites such as acetonitrile and propionitrile, sulfoxides such as dimethyl sulfoxide, or a suitable mixture of them are preferable. In the case of using an acid halogenide as a reactive derivative of carboxylic acid, the reaction can be conducted in the presence of a base, for the purpose of removing liberated hydrohalogenide from the reaction system. As the base, for example, inorganic bases such as sodium carbonate, potassium carbonate and sodium hydrogencarbonate, aromatic amines such as pyridine and lutidine, and tertiary amines such as triethylamine, tripropylamine, tributylamine, cyclohexyldimethylamine, 4-dimethylaminopyridine, N,N-dimethylaniline, N-methylpiperidine, N-methylpyrrolidine and N-methylmorphorine are used. The base is used in an amount of about 0.8 to 5 mol, preferably about 1 to 3 mol, relative to 1 mol of the compound (IX). The reaction time varies with the reagents or solvents employed, it ranges usually from 30 minutes to 24 hours, preferably 30 minutes to 4 hours. The reaction temperature range usually from 0 to 100° C., preferably from 0 to 70° C.

Compound (I) can also be produced, while accompanied by isomerization in the reaction system, by the following procedure, namely, carboxylic acid represented by the formula: $R^3$—COOH ($R^3$ is as defined above) or a reactive derivative thereof is added to the compound (VIII), and the mixture is stirred, under acidic conditions, for a period ranging from 5 minutes to 3 hours, preferably from 10 minutes to 1 hours, at temperatures ranging from 0 to 100° C., preferably from 0 to 70° C., then the reaction mixture is subjected to acylation by adding the above-mentioned base. The carboxylic acid or a reactive derivative thereof is used in an amount usually ranging from about 1.0 to 5.0 mol, preferably from about 1.0 to 2.0 mol, relative to 1 mol of the compound (VIII). This reaction is advantageously conducted in the presence of a solvent inert to the reaction. While any solvent can be employed so long as it does not hamper the proceeding of the reaction, for example, ethers such as diethyl ether, tetrahydrofuran, dioxane and 1,2-dimethoxyethane, hydrocarbons such as benzene, toluene and cyclohexane, amides such as N,N-dimethylformamide and N,N-dimethylacetamide, halogenated hydrocarbons such as dichloromethane, chloroform, carbon tetrachloride and 1,2-dichloroethane, nitriles such as acetonitrile and propionitrile, sulfoxides such as dimethyl sulfoxide, or a suitable mixture of them are preferable. The compound (I) thus produced can be isolated from the reaction mixture by a conventional method, which can readily be purified by means of, for example, recrystallization, distillation and chromatography.

When $R^4$ in the compound (I) is an alkyl group, the compound is subjected to the above-mentioned acylation, followed by conducting alkylation in the presence of a base using a corresponding alkylating agent (e.g. alkyl halide or sulfonic acid ester of alcohol). The alkylating agent is employed, relative to 1 mol of the compound (I), in an amount ranging from about 1.0 to 5.0 mol, preferably from about 1.0 to 2.0 mol. Examples of the base include inorganic bases such as sodium carbonate, potassium carbonate and sodium hydrogencarbonate, aromatic amine such as pyridine and lutidine, tertiary amines such as triethylamine, tripropylamine, tributylamine, cyclohexyl dimethylamine, 4-dimethyl aminopyridine, N,N-dimethyl aniline, N-methyl piperidine, N-methyl pyrrolidine and N-methyl morpholine, alkali metal hydrides such as sodium hydride and potassium hydride, metal amides such as sodium amide, lithium diisopropyl amide and lithium hexamethyl disilazide, and metal alkoxides such as sodium methoxide, sodium ethoxide and potassium tertiary butoxide. The base is used, relative to 1 mol of the compound (I), in an amount ranging from about 1.0 to 5.0 mol, preferably from about 1.0 to 2.0 mol. It is advantageous that this reaction is conducted in the presence of a solvent inert to the reaction. While, as the solvent, any one can be used so long as it does not hamper the proceeding of the reaction, for example, alcohols such as methanol, ethanol and propanol, ethers such as diethyl ether, tetrahydrofuran, dioxane and 1,2-dimethoxyethane, hydrocarbons such as benzene, toluene, cyclohexane and hexane, amides such as N,N-dimethylformamide and N,N-dimethylacetamide, halogenated hydrocarbons such as dichloromethane, chloroform, carbon tetrachloride and 1,2-dichloroethane, nitriles such as acetonitrile and propionitrile, sulfoxides such as dimethyl sufloxide, water, or a suitable mixture of these solvents are preferable. The reaction time ranges usually from 30 minutes to 48 hours, preferably from 30 minutes to 6 hours. The reaction temperature ranges usually from −20 to 200° C., preferably from −10 to 150° C. The product (I) can be isolated from the reaction mixture in accordance with a conventional method, and can be readily purified by means of, for example, recrystallization, distillation and chromatography.

When the compound (I) is a urea compound, it is produced by allowing the compound (VIII) or the compound (IX) to react with an isocyanate. As the isocyanate, for example, a compound represented by the formula: $R^{3'}N=C=O$ [wherein $R^{3'}$ represents a group formed by removing NH from the above-mentioned $R^3$] or a salt thereof is used. Relative to 1 mol of the compound (VIII) or (IX), the isocyanate is used in an amount ranging from about 1.0 to 5.0 mol, preferably from about 1.0 to 2.0 mol. It is advantageous that this reaction is conducted in the presence of a solvent inert to the reaction. While, as the solvent, any one can be used so long as it does not hamper the proceeding of the reaction, for example, hydrocarbons such as benzene, toluene, cyclohexane and hexane, halogenated hydrocarbons such as dichloromethane, chloroform, carbon tetrachloride and 1,2-dichloroethane, ethers such as diethyl ether, tetrahydrofuran, dioxane and 1,2-dimethoxyethane, amides such as N,N-dimethylformamide and N,N-dimethylacetamide, or a suitable mixture of these solvents are preferable. The reaction time ranges usually from 10 minutes to 24 hours, preferably from tO minutes to 4 hours. The reaction temperature ranges usually from 0 to 100° C., preferably from 0 to 70° C.

The compound (X) is produced by subjecting the compound (V) to alkylation, followed by processing with hydrobromic acid. The alkylation is conducted by reacting the compound (V) with a diluted Grignard reagent, which is prepared from cyclopropyl bromide and magnesium, with an inert solvent. Preparation of the Grignard reagent from cyclopropyl bromide can be conducted in accordance with a conventional method. Relative to 1 mol of cyclopropyl bromide, magnesium is used in an amount ranging from about 1.0 to 5.0 mol, preferably from about 1.0 to 1.5 mol. It is advantageous that this reaction is conducted in the presence of a solvent inert to the reaction. While, as the solvent, any one can be used so long as it does not hamper the proceeding of the reaction, for example, aromatic hydrocarbons such as benzene and toluene, saturated hydrocarbons such as cyclohexane and hexane, ethers such as tetrahydrofuran, dioxane and 1,2-dimethoxyethane, amides such as N,N-dimethylformamide and N,N-dimethylacetamide, sulfoxides such as dimethyl sulfoxide, or a suitable mixture thereof. The reaction time ranges usually from 10 minutes to 10 hours, preferably from 15 minutes to 3 hours. The reaction temperature ranges usually from 0 to 150° C., preferably from 40 to 80° C. The reaction may be conducted by optionally allowing a small amount of iodine to exist in the reaction system. The Grignard reagent formed after termination of the reaction is left standing at room temperature to complete the reaction, then, the solvent is distilled off, or, without distilling off the solvent, the reaction mixture is diluted by adding the solvent, followed by adding dropwise the compound (V) to allow the reaction to proceed. The compound (V) is used, relative to 1 mol of the Grignard reagent, in an amount of about 0.4 to 3.0 mol, preferably about 0.4 to 1.0 mol. While, as the solvent to be used for dilution, any one can be employed so long as it does not hamper the proceeding of the reaction, for example, aromatic hydrocarbons such as benzene and toluene, saturated hydrocarbons such as cyclohexane and hexane, halogenated hydrocarbons such as chlorotoluene, ethers such as tetrahydrofuran, dioxane and 1,2-dimethoxyethane, amides such as N,N-dimethylformamide and N,N-dimethylacetamide, sulfoxides such as dimethyl sufloxide, or a suitable mixture of them. The volume of the solvent to be employed for the dilution ranges, relative to the Grignard reagent, from about 1.0 to 30 times, preferably from about 1.0 to 15 times, as much. The reaction time ranges usually from 10 minutes to 10 hours, preferably from 15 minutes to 3 hours. The reaction temperature ranges usually from 0 to 150° C., preferably from 40 to 100° C. While the product can be used for the subsequent reaction in the state of the reaction mixture or a crude product, it can be isolated from the reaction mixture in accordance with a conventional method, and can be readily purified by means of, for example, recrystallization, distillation and chromatography. The amount of hydrobromic acid to be employed ranges, relative to 1 mol of the compound (V), from about 1.0 to 30 mol, preferably from about 1.0 to 5.0 mol. It is advantageous to carry out this reaction in the presence of a solvent inert to the reaction. While, as the solvent, any one can be employed so long as it does not hamper the proceeding of the reaction, for example, alcohols such as methanol, ethanol and propanol, organic acids such as formic acid and acetic acid, hydrocarbons such as benzene, toluene, cyclohexane and hexane, amides such as N,N-dimethylformamide and N,N-dimethylacetamide, sulfoxides such as dimethyl sulfoxide, water, or a suitable mixture of them, are preferable. The reaction time ranges usually from 1 to 60 hours, preferably from 1 to 15 hours. The reaction temperature ranges usually from 0 to 200° C., preferably from 0 to 80° C. While the product (X) can be used for the subsequent reaction in the state of the reaction mixture or a crude product, it can be isolated from the reaction mixture in accordance with a conventional method, and can be readily purified by means of, for example, recrystallization, distillation and chromatography.

The compound (XI) is produced by allowing the compound (X) to react with potassium phthalimide. The potassium phthalimide is used, relative to 1 mol of the compound (X), in an amount of about 1.0 to 5.0 mol, preferably about 1.0 to 1.5 mol. Condensation of the compound (X) and potassium phthalimide is advantageously conducted in the absence of solvent or in the presence of an inert solvent and, when desired, in the presence of a base. Examples of the base include inorganic bases such as sodium carbonate, potassium carbonate and sodium hydrogencarbonate, aromatic amine such as pyridine and lutidine, tertiary amines such as triethylamine, tripropylamine, tributylamine, cyclohexyl dimethylamine, 4-dimethyl aminopyridine, N,N-dimethyl aniline, N-methyl piperidine, N-methyl pyrrolidine and N-methyl morpholine, alkali metal hydrides such as sodium hydride and potassium hydride, metal amides such as sodium amide, lithium diisopropyl amide and lithium hexamethyl disilazide, and metal alkoxides such as sodium methoxide, sodium ethoxide and potassium tertiary butoxide. The base is used, relative to 1 mol of the compound (X), in an amount ranging from about 1.0 to 5.0 mol, preferably from about 1.0 to 2.0 mol. Examples of the solvent include alcohols such as methanol, ethanol and propanol, ethers such as diethyl ether, tetrahydrofuran, dioxane and 1,2-dimethoxyethane, hydrocarbons such as benzene, toluene, cyclohexane and hexane, amides such as N,N-dimethylformamide and N,N-dimethylacetamide, halogenated hydrocarbons such as dichloromethane, chloroform, carbon tetrachloride and 1,2-dichloroethane, nitriles such as acetonitrile and propionitrile, sulfoxides such as dimethyl sufloxide, or a suitable mixture of these solvents. The reaction time ranges usually from 30 minutes to 20 hours, preferably from 30 minutes to 8 hours. The reaction temperature ranges usually from 0 to 150° C., preferably from 20 to 100° C. While the product (XI) can be used for the subsequent reaction in the state of the reaction mixture or as a crude product, it can be isolated from the reaction mixture in accordance with a conventional method, and can be readily purified by means of, for example, recrystallization, distillation and chromatography.

The compound (XII) is produced by allowing the compound (X) to react with a cyano compound. As the cyano compound, for example, sodium cyanide, potassium cyanide or a mixture of them is used. Or, in the reaction system, hydrogen cyanide may be allowed to react with an alkali metal salt such as sodium hydroxide, potassium hydroxide, sodium carbonate and potassium carbonate to prepare the cyano compound. The cyano compound is used, relative to 1 mol of the compound (X), in an amount ranging from about 0.8 to 10 mol, preferably from about 1.0 to 2.0 mol. This substitution reaction is advantageously conducted in the presence of a solvent inert to the reaction. While, as the solvent, any one can be used so long as it does not hamper the proceeding of the reaction, for example, ethers such as diethyl ether, tetrahydrofuran, dioxane and 1,2-dimethoxyethane, hydrocarbons such as benzene, toluene, cyclohexane and hexane, amides such as N,N-dimethylformamide and N,N-dimethylacetamide, halogenated hydrocarbons such as dichloromethane, chloroform, carbon tetrachloride and 1,2-dichloroethane chlorobenzene and ortho-dichlorobenzene, sulfoxides such as dimethyl sufloxide, or a suitable mixture of these solvents are preferable. Depending on cases, the reaction may be conducted, in the presence of a phase-transfer catalyst, by using water and any of the above-mentioned organic solvents insoluble or hardly soluble in water. As the phase-transfer catalyst, for example, quaternary ammonium salts such as tetrabutylammonium bromide and benzyltriethylammonium chloride, and quaternary phosphonium salts are used. The amount of the phase-transfer catalyst to be employed ranges, relative to 1 mol of the compound (X), from about 0.001 to 10 mol, preferably from about 0.005 to 0.5 mol. The reaction time ranges usually from 30 minutes to 20 hours, preferably from 30 minutes to 8 hours. The reaction temperature ranges usually from 0 to 200° C., preferably from 20 to 150° C. While the compound (XII) can optionally be used for the subsequent reaction in the state of the reaction mixture or as a crude product, it can be isolated from the reaction mixture in accordance with a conventional method, which can be readily purified by means of, for example, recrystallization, distillation and chromatography.

The compound (IX) is produced by subjecting the compound (XI) to deprotection. Relative to 1 mol of the compound (XI), usually about 1.0 to 20 mol, preferably about 1.0 to 5.0 mol, of, for example, amines such as methylamine and ethylamine, hydrazines such as hydrazine and phenylhydrazine, alkali sulfides such as sodium sulfide and potassium sulfide or mineral acids such as hydrochloric acid and sulfuric acid, are preferably employed. This reaction is advantageously conducted in the presence of a solvent inert to the reaction. While, as the solvent, any one can be employed so long as it does not hamper the proceeding of the reaction, for example, alcohols such as methanol, ethanol and propanol, ethers such as diethyl ether, tetrahydrofuran, dioxane and 1,2-dimethoxyethane, hydrocarbon such as benzene, toluene, cyclohexane and hexane, amides such as N,N-dimethylformamide and N,N-dimethylacetamide, sulfoxides such as dimethyl sulfoxide, or a suitable mixture of them are preferable. The reaction time ranges usually from 30 minutes to 12 hours, preferably from 30 minutes to 5 hours. The reaction temperature ranges usually from 0 to 200° C., preferably from 20 to 100° C. While the product (IX) can optionally be used in the subsequent reaction in the state of the reaction mixture or a crude product, it can be isolated from the reaction mixture in accordance with a conventional method, and can be purified by means of, for example, recrystallization, distillation and chromatography. And, the compound (IX) can also be produced by reducing the cyano group of the compound (XII), in accordance with substantially the same procedure as in the production of the compound (VIII) from the compound (VII).

The configurational isomers (E-, Z-compounds) of the above-mentioned compounds (VII) and (VIII) can be isolated and purified, when the isomerization occurs, by conventional separating means such as extraction, recrystallization, distillation and chromatography, to give pure compounds. Or, in accordance with the methods described on pp.251–253 of Shin Jikken Kagaku Koza 14 (compiled by The Chemical Society of Japan) or pp.273–274 of The 4th Edition Jikken Kagaku Koza 19 (compiled by The Chemical Society of Japan) and methods analogous to those methods, isomerization of the double bond is allowed to proceed by heating, using an acid catalyst, a transition metal complex, a metal catalyst, a free-radical seed catalyst, light irradiation or a strong basic catalyst, to give corresponding pure isomers.

Depending on the kinds of substituents of the compound (I), steric isomers are produced, and not only these isomers singly but also a mixture of them are included in the present invention.

In the above-mentioned reaction steps, when desired, conventional deprotection reaction, acylation, alkylation, hydrogenation, oxidation, reduction, carbon-chain elongation and substituent-exchange reaction are conducted singly or by combining two or more of them to synthesize the compound (I). These reactions are conducted in accordance with the method described in, for example, "Shin Jikken Kagaku Koza Vol.14, 15, compiled by The Chemical Society of Japan, Issued in the years of Showa 52, 53".

In the respective reaction of this invention and the respective reactions of synthesizing the starting compounds as described above, in the case where the starting compounds have, as the substituents, amino group, carboxyl group or hydroxyl group, such protective groups as generally employed in the peptide chemistry may optionally be introduced into these groups, and, by removing the protective groups after the reaction depending on necessity, the object compound can be obtained.

Examples of the amino-protective groups include formyl group, $C_{1-6}$ alkyl-carbonyl groups (e.g. acetyl and propionyl), $C_{1-6}$ alkyloxycarbonyl groups (e.g. methoxycarbonyl and ethoxycarbonyl), benzoyl group, $C_{7-10}$ aralkyl-carbonyl groups (e.g. benzylcarbonyl), trityl group, phthaloyl group and N,N-dimethylaminomethylene group. These groups may optionally be substituted with 1 to 3 halogen atoms (e.g. fluorine, chlorine, bromine and iodine) and nitro group.

Examples of the carboxyl-protective groups include $C_{1-6}$ alkyl groups (e.g. methyl, ethyl, propyl, isopropyl, butyl and tert-butyl), phenyl group, trityl group, and silyl group. These groups may optionally be substituted with 1 to 3 halogen atoms (e.g. fluorine, chlorine, bromine and iodine), formyl group, $C_{1-6}$ alkyl-carbonyl groups (e.g. acetyl, propionyl and butylyl) and nitro group.

Examples of the hydroxyl-protective groups include $C_{1-6}$ alkyl groups (e.g. methyl, ethyl, propyl, isopropyl, butyl and tert-butyl), phenyl group, $C_{7-10}$ aralkyl groups (e.g. benzyl), $C_{1-6}$ alkyl-carbonyl groups (e.g. acetyl and propionyl), benzoyl group, $C_{7-10}$ aralkyl-carbonyl groups (e.g. benzylcarbonyl), tetrahydropyranyl group, tetrahydrofuranyl group and silyl group. These groups may optionally be substituted with 1 to 3 halogen atoms (e.g. fluorine, chlorine, bromine and iodine), $C_{1-6}$ alkyl groups (e.g. methyl, ethyl and propyl), phenyl group, $C_{7-10}$ aralkyl groups (e.g. benzyl) and nitro group.

For removing these protective groups, per se known methods or methods analogous thereto, as exemplified by methods using an acid, a base, ultraviolet ray, hydrazine, phenylhydrazine, sodium N-methyl dithiocarbamate, tetrabutyl ammonium fluoride and palladium acetate, and reduction.

The compound (I) of this invention can be isolated and purified by a conventional means such as solvent-extraction, pH adjustment, phasic transfer, crystallization, recrystallization and chromatography. And, while the starting compounds for producing the compound (I) of this invention, or salts thereof can be isolated and purified by substantially the same conventional means as mentioned above, these compounds may optionally be used as the subsequent reaction step in the state of the reaction mixture without isolation.

In the case where the object compound is obtained in the free form by the above-mentioned reaction, it may optionally be converted to the corresponding salt by a conventional method, and, in the case where the object compound is obtained as a salt, it may optionally be converted to its free form or any other salt by a conventional method. Thus-produced compound (I) can be isolated from the reaction mixture and purified by a conventional means such as phasic transfer, concentration, solvent-extraction, fractional distillation, crystallization, recrystallization and chromatography.

In the case where the compound (I) exists as, for example, a configurational isomer, diastereomer or conformer, it may optionally be isolated respectively by the above-mentioned isolating and purifying means. When the compound (I) is an optically active compound, it can be resolved into d-isomer and l-isomer by a conventional means of optical resolution.

The compound (I) of this invention or the compound ($I^a$) shows a high binding affinity for melatonin receptor, and is less in toxicity and undesirable side effects, which is thus useful as a medicine.

The compound (I) of this invention or the compound (I$^a$) acts, as a melatonin agonist or antagonist on mammals (e.g. mouse, rat, hamster, rabbit, cat, dog, cow, sheep, monkey and humans) and is therefore useful for producing compositions having a binding affinity for melatonin receptor, especially as a melatonin receptor agonistic composition, and it can be used for the therapy of diseases, including circadian rhythm disorders, possibly affected by melatonin, for example, sleep-wake rhythm disorders, jet lag, shift-work syndrome, seasonal melancholia, disorders in reproduction and neurosecretion, senile dementia, Alzheimer's disease, various disorders accompanied with aging (e.g. senility-resist), cerebral circulation disorders, stress, epilepsy, convulsion, anxiety, depression, parkinsonism, hypertension, glaucoma, cancer, insomnia and diabetes mellitus, and is also effective on immunomodulation, nootropic, mental stability or ovulation control (e.g. contraception). The compound (I) of this invention or the compound (I$^a$) is used as, for example, a circadian rhythm regulating agent, preferably a therapeutic agent of sleeping disturbance (e.g. a sleep-inducing agent), a regulating agent of sleep-awake rhythm (including sleep-awake rhythm adjusting action), or a therapeutic agent of a time zone change syndrome, so-called jet lag.

The compound (I) of this invention and the compound (I$^a$) are less in toxic, and can be safely administered orally or non-orally (e.g. topical, rectal or intravenous) as is, or as a pharmaceutical composition mixed with a pharmaceutically acceptable carrier in accordance with a per se known method, for example, tablets (including sugar-coated tablets, film-coated tablets), powdery preparations, granular preparations, capsules (including soft capsules), liquid preparations, injectable preparations, suppositories, sustained-release preparations, pasting preparations, and as chewing gum. The content of the compound (I) or the compound (I$^a$) in the pharmaceutical preparation of this invention is dependent on, for example, type of prepalations, administration method and carriers. It usually ranges from about 0.01 to nearly 100 weight % relative to the whole weight of the preparation. The dosage is dependent on, for example, the subject, administration route and type of diseases, and, it is administered, when administered orally to, for example, an adult patient suffering from sleep disturbances once or a few times daily, in an amount ranging from about 0.1 to about 20 mg/kg body weight in terms of the effective component, i.e. compound (I) or the compound (I$^a$), preferably from about 0.2 to about 10 mg/kg body weight, more preferably from about 0.5 to about 10 mg/kg body weight. The compound may optionally be used with any further effective components (e.g. benzodiazepine type drugs such as benzodiazepine compounds including triazolam, diazepam, alprazolam and estazolam; circadian rhythm regulating agents, e.g. fatty acid derivatives such as butoctamide or a salt thereof; and sleep-inducing substances such as cis-9,10-octadecenoamide). Such other effective components as mentioned above are admixed with the compound (I) or the compound (I$^a$) in accordance with a per se known method, and the mixture may optionally be used concurrently as a pharmaceutical composition [e.g. tablets, powdery products, granules, capsules (including soft capsules), liquid preparations, injectable preparations, suppositories and sustained-release preparations].

As pharmaceutically acceptable carriers to be employed for the preparations of this invention, mention is made of various organic or inorganic carriers conventionally used as materials for preparing pharmaceutical compositions, for example, excipients, lubricants, binders and disintegrants in solid preparations; and solvents, solubilizers, suspending agents, isotonizing agents, buffering agents and soothing agents. And, depending on necessity, conventional additives such as antiseptics, antioxidants, coloring agents, sweetening agents, absorbants and wetting agents can also be employed.

As the excipient, mention is made of, for example, lactose, sucrose, D-mannitol, starch, corn starch, crystalline cellulose and more volatile silicic acid anhydride.

As the lubricant, mention is made of, for example, magnesium stearate, calcium stearate, talc and colloid silica.

As the binder, mention is made of, for example, crystalline cellulose, sugar, D-mannitol, dextrin, hydroxypropyl cellulose, hydroxypropyl methyl cellulose, polyvinylpyrrolidone, starch, sucrose, gelatin, methyl cellulose, carboxymethyl cellulose sodium.

As the disintegrant, mention is made of, for example, starch, carboxymethyl cellulose, carboxymethyl cellulose calcium, crosscarmellose sodium, carboxymethyl starch sodium and L-hydroxypropyl cellulose.

As the solvent, mention is made of, for example, water for injection, alcohol, propylene glycol, macrogol, sesame oil, corn oil and olive oil.

As the solubilizer, mention is made of, for example, polyethylene glycol, propylene glycol, D-mannitol, benzyl benzoate, ethanol, trisaminomethane, cholesterol, triethanolamine, sodium carbonate and sodium citrate.

As the suspending agent, mention is made of, for example, a surfactant such as stearyl triethanol amine, sodium lauryl sulfate, lauryl aminopropionic acid, lecitin, benzalconium chloride, benzetonium chloride and glycerin monostearate; and hydrophilic polymer such as polyvinyl alcohol, polyvinyl pyrrolidone, carboxymethyl cellulose sodium, methyl cellulose, hydroxymethyl cellulose, hydroxyethyl cellulose and hydroxypropyl cellulose.

As the isotonizing agent, mention is made of, for example, glucose, D-sorbitol, sodium chloride, glycerin and D-mannitol.

As the buffering agent, mention is made of, for example, a buffer solution of phosphate, acetate, carbonate and citrate.

As the soothing agent, mention is made of, for example, benzyl alcohol.

As the antiseptic, mention is made of, for example, para-oxybenzoic acid esters, chlorobutanol, benzyl alcohol, phenethyl alcohol, dehydroacetic acid and sorbic acid.

As the antioxidant, mention is made of, for example, sulfite, ascorbic acid and α-tocopherol.

BEST MODE FOR CARRYING OUT THE INVENTION

EXAMPLES

The present invention will be described in further detail by the following Reference Examples, Working Examples and Experimental Examples, but they are mere examples and are not intended by way of limitation upon the scope of this invention, and they may be modified within the range which does not deviate the scope of this invention. "Room temperatures" in the following Reference Examples, Formulation Examples and Working Examples mean usually 10° C. to 35° C. "%" means weight % unless otherwise specified.

Other abbreviations employed in the description have the following meanings.

s: singlet d: doublet t: triplet
q: quartet
m: multiplet
br: broad
J: coupling constant
Hz: Herz
CDCl$_3$: deuterochloroform
d$_6$-DMSO: (dimethyl sulfoxide)-d$_6$
NMR: proton nuclear magnetic resonance Reference Example 1

(E)-(6-methoxy-2-phenylindan-1-ylidene)acetonitrile

To a solution of 1,1,1,3,3,3-hexamethyldisilazane (2.19 g, 13.6 mmol.) in tetrahydrofuran (80 ml) was gradually added dropwise, under argon atmosphere at −78° C., a normal butyl lithium hexane solution (1.56 M, 8.72 ml, 13.6 mmol.). The mixture was stirred for 10 minutes, to which was then added dropwise acetonitrile (0.65 ml, 12.4 mmol.). The mixture was stirred for further 20 minutes, to which was added dropwise a solution of 6-methoxy-2-phenyl-1-indanone (2.70 g, 11.3 mmol.) in tetrahydrofuran (10 ml), and the mixture was stirred for one hour. The temperature of the reaction mixture was gradually reverted to room temperature while pouring water thereto, and the organic substance was extracted with ethyl acetate. The extract solution was washed with a saturated aqueous saline solution and water, dried over anhydrous magnesium sulfate, followed by distilling off the solvent under reduced pressure. The residue was dissolved in toluene (100 ml), to which was added 10-camphor-sulfonic acid (0.5 g). The reaction mixture was heated for 2 hours under reflux. The reaction mixture was poured into a saturated aqueous solution of sodium hydrogencarbonate, and the organic substance was extracted with ethyl acetate. The extract solution was washed with a saturated aqueous saline solution and water, dried over anhydrous magnesium sulfate, then the solvent was distilled off under reduced pressure. The residue thus obtained was recrystallized to afford the titled compound (yield 0.47 g, yield 16%).

m.p. 112–114° C. (recrystallized from ethyl acetate/isopropyl ether). NMR(CDCl$_3$) δ: 3.03(1H,d,J=17 Hz), 3.59 (1H,dd,J=8.2&17 Hz), 3.86(3H,s), 4.49(1H,dd,J=8.2 Hz), 5.69(1H,d,J=2.6 Hz), 6.95–7.32(8H,m).

Reference Example 2

2-(5-Methoxy-2-phenyl-1H-inden-3-yl)ethylamine hydrochloride

To a solution of (E)-(6-methoxy-2-phenylindan-1-ylidene)acetonitrile (0.45 g, 1.72 mmol.) in ethanol (30 ml) were added a saturated ammonia/ethanol solution (10 ml) and Raney cobalt (0.3 g). The mixture was stirred for 10 hours at 10 hours at room temperature under hydrogen atmosphere (5 kgf/cm$^2$). The Raney cobalt was filtered off, then the solvent was filtered off under reduced pressure to leave 2-(6-methoxy-2-phenylindan-1-ylidene)ethylamine., which was dissolved in a hydrogen chloride/ethanol solution. The solvent was then distilled off under reduced pressure to afford the titled compound (0.3 g, yield 58%). This compound was used for the subsequent reaction without further purification.

Reference Example 3

4-(3-Bromopropyl)-1,2-dihydro-6-methoxynaphthalene

To tetrahydrofuran (100 ml), in which magnesium (2.9 g) was suspended, was gradually added dropwise under ice-cooling bromocyclopropane (14.4 g, 119 mmol.) under argon atmosphere. The mixture was stirred for 30 minutes at room temperature, to which was added dropwise a tetrahydrofuran (50 ml) solution of 7-methoxy-1-tetralone (15 g, 85.1 mmol.), which was heated for 2 hours under reflux. The reaction mixture was cooled to room temperature, to which was poured a saturated aqueous solution of ammonium chloride, followed by extracting the organic substance with ethyl acetate. The extract solution was washed with a saturated aqueous saline solution and water, which was dried over anhydrous magnesium sulfate, followed by distilling off the solvent under reduced pressure. The residue was dissolved in acetic acid (100 ml), to which was added 20% hydrobromic acid (75 ml). The reaction mixture was stirred overnight at room temperature. The reaction mixture was concentrated, which was poured into a saturated aqueous solution of sodium hydrogencarbonate, and the organic substance was extracted with ethyl acetate. The extract solution was washed with a saturated aqueous saline solution and water, which was dried over anhydrous magnesium sulfate, followed by distilling off the solvent under reduced pressure. The residue was purified by means of a silica gel column chromatography (ethyl acetate hexane=1:9) to afford the titled compound (20 g, yield 84%, oily).

NMR(CDCl$_3$) δ: 2.00–2.15(2H,m), 2.17–2.30(2H,m), 2.55–2.70(4H,m), 3.45(2H,t,J=6.6 Hz), 3.80(3H,s), 5.94 (1H,t,J=4.4 Hz), 6.69(1H,dd,J=2.6&8.1 Hz), 6.83(1H,d,J= 2.6 Hz), 6.07(1H,d,J=8.1 Hz). Elemental analysis for C$_{14}$H$_{17}$BrO: Calcd.: C, 59.80; H, 6.09. Found: C, 59.77; H, 6.32.

Reference Example 4

2-[3-(7-Methoxy-3,4-dihydronaphthalen-1-yl) propyl]isoindole-1,3-dione

A mixture of 4-(3-bromopropyl)-1,2-dihydro-6-methoxynaphthalene (10 g, 35.6 mmol.) and potassium phthalimide (7.9 g, 42.7 mmol.) was stirred in N,N-dimethylformamide (50 ml) for one hour at 100° C. The reaction mixture was cooled to room temperature, to which was poured water, then the organic substance was extracted with ethyl acetate. The extract solution was washed with a saturated aqueous saline solution and water, which was dried over anhydrous magnesium sulfate, then the solvent was distilled off under reduced pressure. The residue thus obtained was purified by means of a silica gel column chromatography (ethyl acetate:hexane=2:8) to afford the titled compound (11.8 g, yield 95%, oily).

NMR(CDCl$_3$) δ: 1.95(2H,m), 2.12–2.27(2H,m), 2.48(2H, t,J=7.7 Hz), 2.63(2H,t,J=7.7 Hz), 3.70– 3.93(5H,m), 5.92 (1H,t,J=4.6 Hz), 6.67(1H,dd,J=2.6&8.1 Hz), 6.78(1H,d,J= 2.6 Hz), 7.03(1H,d,J=8.1 Hz), 7.65–7.90(4H,m). Elemental analysis for C$_{22}$H$_{21}$NO$_3$: Calcd.: C, 76.06; H, 6.09; N, 4.03. Found: C, 76.23; H, 6.23; N, 3.99.

Reference Example 5

3-(7-Methoxy-3,4-dihydronaphthalen-1-yl) propylamine

A mixture of 2-[3-(7-methoxy-3,4-dihydronaphthalen-1-yl)propyl]isoindole-1,3-dione (11.8 g, 34.0 mmol.) and hydrazine monohydrate (5.1 g, 0.1 mol.) was heated in ethanol (150 ml) for one hour under reflux. The reaction mixture was ice-cooled, then resulting insolubles were filtered off. The filtrate was concentrated under reduced pressure to afford the titled compound (5.7 g, yield 77%, oily).

This compound was used for the subsequent reaction without further purification.

NMR(CDCl$_3$) δ: 1.68(2H,m), 2.15–2.30(2H,m), 2.46(2H, t,J=7.5 Hz), 2.60–2.80(4H,m), 3.80(3H,s), 5.89(1H,t,J=4.4 Hz), 6.68(1H,dd,J=2.4&8.2 Hz), 6.83(1H,d,J=2.4 Hz), 7.06 (1H,d,J=8.2 Hz), 2H of NH$_2$ was too broad to confirm.

Reference Example 6

4-(7-Methoxy-3,4-dihydronaphthalen-1-yl)butyronitrile

A mixture of 4-(3-bromopropyl)-1,2-dihydro-6-methoxynaphthalene (10 g, 35.6 mmol.) and sodium cyanide (1.92 g, 39.1 mmol.) was stirred in dimethyl sulfoxide (20 ml) for one hour at room temperature. The reaction mixture was poured into water, then the organic substance was extracted with ethyl acetate. The extract solution was washed with a saturated aqueous saline solution and water, which was dried over anhydrous magnesium sulfate, followed by distilling off the solvent under reduced pressure. The residue thus obtained was purified by means of a silica gel column chromatography (ethyl acetate:hexane=1:9) to afford the titled compound. (7.5 g, yield 93%, oily).

NMR(CDCl$_3$) δ: 1.80–1.98(2H,m), 2.18–2.30(2H,m), 2.35(2H,t,J=7.0 Hz), 2.50–2.75(4H,m), 3.80(3H,s), 5.95 (1H,t,J=4.6 Hz), 6.70(2H,dd,J=2.6&8.1 Hz), 6.78(1H,d,J= 2.6 Hz), 7.07(1H,d,J=8.1 Hz). Elemental analysis for C$_{15}$H$_{17}$NO: Calcd.: C, 79.26; H, 7.54; N, 6.16. Found: C, 79.23; H, 7.66; N, 6.36.

Reference Example 7

4-(7-Methoxy-3,4-dihydronaphthalen-1-yl)butylamine

By substantially the same procedure as in Reference Example 2, the titled compound was produced from 4-(7-methoxy-3,4-dihydronaphthalen-1-yl)butyronitrile (yield 90%, oily).

NMR(d$_6$-DMSO) δ: 1.30–1.60(4H,m), 2.05–2.67(10H, m), 3.73(3H,s), 5.87(1H,t,J=4.0 Hz), 6.70(1H,dd,J=2.0&8.1 Hz), 6.76(1H,d,J=2.0 Hz), 7.05(1H,d,J=8.1 Hz).

Reference Example 8

(E)-(6-methoxyindan-1-ylidene)acetonitrile

To a suspension of 60% sodium hydride (2.71 g, 67.9 mmol.) in tetrahydrofuran (150 ml) was added dropwise, under ice-cooling, diethyl cyanomethylphosphonate (11.5 g, 64.8 mmol.). The mixture was stirred for 15 minutes. To the reaction mixture was added dropwise a solution of 6-methoxy-1-indanone (10.0 g, 61.7 mmol.) in tetrahydrofuran (30 ml). The reaction mixture was stirred for 30 minutes at room temperature, which was poured into water, and then the organic substance was extracted with ethyl acetate. The extract solution was washed with a saturated aqueous saline solution and water, which was then dried over anhydrous magnesium sulfate, followed by distilling off the solvent under reduced pressure. The residue thus obtained was purified by means of a silica gel column chromatography (ethyl acetate:hexane=2:8), followed by recrystallization from ethyl acetate/hexane to afford the titled compound (6.00 g, yield 53%), m.p.95–96° C. (recrystallized from ethyl acetate/hexane).

NMR(CDCl$_3$) δ: 3.01–3.18(4H,m), 3.83(3H,s), 5.61(1H, t,J=2.4 Hz), 6.96–7.03(2H,m), 7.27(1H,d,J=8.8 Hz).

Reference Example 9

(E)-2-(6-methoxyindan-1-ylidene)ethylamine

To a solution of (E)-(6-methoxyindan-1-ylidene) acetonitrile (1.60 g, 8.64 mmol.) in ethanol (80 ml) were added a 2M ammonia/methanol solution (40 ml) and Raney cobalt (1.6 g). The reaction mixture was stirred, under hydrogen atmosphere (4 kgf/cm$^2$) for 32 hours at 40° C. and for further 8 hours at 70° C. The Raney cobalt was filtered off, and then the solvent was distilled off. The residue was purified by means of a silica gel column chromatography (chloroform:methanol=9:1 to chloroform:methanol:triethylamine=90:8:2) to afford the titled compound (1.40 g, yield 86%, oily).

NMR(CDCl$_3$) δ: 2.70–2.80(2H,m), 2.89–2.97(2H,m), 3.48(2H,d,J=6.6 Hz), 3.81(3H,s), 5.91–6.01(1H,m), 6.77 (1H,dd,J=2.4&8.2 Hz), 6.96(1H,d,J=2.4 Hz), 7.13(1H,d,J= 8.2 Hz), 2H of NH$_2$ was too broad to confirm.

Reference Example 10

3-(3-Bromo-4-methoxyphenyl)propionic acid

To a solution of 3-(4-methoxyphenyl)propionic acid (4.0 g, 22.2 mmol) in acetic acid (20 ml) was added bromine (3.9 g, 24.4 mmol) gradually dropwise at 10° C. and the mixture was stirred at room temperature for 30 minutes. This reaction mixture was diluted with water and extracted with ethyl acetate. The extract was washed serially with saturated saline and water and dried over anhydrous magnesium sulfate and the solvent was distilled off under reduced pressure. The residue was washed with hexane to provide the title compound (yield 5.0 g, 87%).

m.p. 94–96% NMR(CDCl$_3$) δ: 2.64(2H,t,J=7.8 Hz), 2.88 (2H,t,J=7.8 Hz), 3.87(3H,s), 6.82(1H,d,J=8.6 Hz), 7.11(1H, dd,J=2.2 Hz,8.6 Hz), 7.39(1H,d,J=2.2 Hz), 9.15(1H,br s). Elemental analysis for C$_{10}$H$_{11}$BrO$_3$: Calcd.: C, 46.36; H, 4.28. Found: C, 46.66; H, 4.21.

Reference Example 11

5-Bromo-6-methoxy-1-indanone 3-(3-Bromo-4-methoxyphenyl)propionic acid (5.0 g, 19.3 mmol) and thionyl chloride (10 ml) were refluxed for 1 hour. This reaction mixture was concentrated under reduced pressure to remove the excess thionyl chloride and the residue was dissolved in 1,2-dichloroethane (50 ml). To this solution was added aluminum chloride (2.8 g, 20.8 mmol) over 10 minutes on an ice bath and the mixture was further stirred at room temperature for 1 hour. This reaction mixture was poured in iced water and extracted with ethyl acetate. The extract was washed serially with saturated saline and water and dried over anhydrous magnesium sulfate and the solvent was distilled off under reduced pressure. The residue was washed with hexane to provide the title compound (yield 4.3 g, 92%).

m.p. 149–151° C. NMR(CDCl$_3$) δ: 2.63–2.71(2H,m), 3.02–3.15(2H,m), 3.93(3H,s), 7.19(1H,s), 7.70(1H,s). Elemental analysis for C$_{10}$H$_9$BrO$_2$: Calcd.: C, 49.82; H, 3.76; Br, 33.14. Found: C, 49.77; H, 3.71; Br, 32.95.

Reference Example 12

(E)-(5-Bromo-6-methoxyindan-1-ylidene)acetonitrile

Using 5-bromo-6-methoxy-1-indanone and diethyl cyanomethylphosphate, the procedure of Reference Example 8 was otherwise repeated to provide the title compound (yield 75%).

m.p. 180–182° C. NMR(CDCl$_3$) δ: 3.00–3.18(4H,m), 3.92(3H,s), 5.63(1H,t, J=2.4 Hz), 6.94(1H,s), 7.56(1H,s). Elemental analysis for C$_{12}$H$_{10}$BrNO: Calcd.: C, 54.57; H, 3.82; N, 5.30; Br, 30.25. Found: C, 54.40; H, 3.96; N, 5.15; Br, 30.10.

Reference Example 13

(E)-2-(5-Bromo-6-methoxyindan-1-ylidene) ethylamine

Starting with (E)-(5-bromo-6-methoxyindan-1-ylidene) acetonitrile, the title compound was synthesized in otherwise the same manner as Reference Example 9 (yield 95%; oil).

NMR(CDCl$_3$) δ: 2.70–2.80(2H,m), 2.85–3.00(2H,m), 3.47(2H,d,J=7.0 Hz), 3.90(3H,s), 5.98(1H,m), 6.95(1H,s), 7.41(1H,s).

Reference Example 14

2-(6-Bromo-5-methoxy-1H-inden-3-yl)ethylamine hydrochloride (E)-2-(5-Bromo-6-methoxyindan-1-ylidene)ethylamine (5.0 g, 18.6 mmol) was dissolved in saturated HCl/ethanol (200 ml) and the solution was refluxed for 2 hours. After cooling, the solvent was distilled off under reduced pressure and the resulting crystals were washed with diethyl ether to provide the title compound (yield 4.61 g, 81%).

m.p. 244–247° C. (as recrystallized from ethanol) NMR (d$_6$-DMSO) δ: 2.89(2H,t,J=7.1 Hz), 3.00–3.15(2H,m), 3.31 (2H,s), 3.92(3H,s), 6.46(1H,s), 7.24(1H,s), 7.65(1H,s), 8.16 (2H, br s).

Reference Example 15

2-Benzylidene-6-methoxy-1-indanone

6-Methoxy-1-indanone (10 g, 61.2 mmol), benzaldehyde (7.85 g, 74.0 mmol), piperidine (1.05 g, 12.3 mmol), and acetic acid (4.4 g, 74.0 mmol) were refluxed in toluene (150 ml) for 3 hours. After the reaction mixture was cooled to room temperature, the solvent was distilled off under reduced pressure. The residue was diluted with water and extracted with ethyl acetate. The extract was washed serially with saturated saline and water and dried over anhydrous magnesium sulfate and the solvent was distilled off under reduced pressure. The resulting crystals were washed with diethyl ether to provide the title compound (yield 2.3 g, 80%).

m.p. 131–133° C. NMR(CDCl$_3$) δ: 3.87(3H,s), 3.99(2H, s), 7.21(1H,dd,J=2.6 Hz,8.1 Hz), 7.36(1H,d,J=2.6 Hz), 7.37–7.72(7H,m).

Reference Example 16

2-Benzyl-6-methoxy-1-indanone

To a solution of 2-benzylidene-6-methoxy-1-indanone (12.25 g, 48.9 mmol) in ethanol (500 ml) was added 10% hydrous palladium-carbon (1.5 g) and catalytic reduction was carried out in a hydrogen stream at atmospheric temperature and pressure. The palladium-carbon was then filtered off and the filtrate was concentrated under reduced pressure. The residue was purified by silica gel column chromatography (ethyl acetate-hexane=2:8) to provide the title compound (yield 11.26 g, 92%; oil).

NMR(CDCl$_3$) δ: 2.60–3.20(4H,m), 3.39(1H,dd,J=3.8 Hz,13.9 Hz), 3.84(3H,s), 7.12–7.39(8H,m).

Reference Example 17

(E)-(2-Benzyl-6-methoxyindan-1-ylidene) acetonitrile

Starting with 2-benzyl-6-methoxy-1-indanone and acetonitrile, the title compound was synthesized in otherwise the same manner as Reference Example 1 (yield 76%). This compound was used in the next reaction without further purification.

Reference Example 18

(E)-2-(2-Benzyl-6-methoxyindan-1-ylidene) ethylamine

Starting with (E)-(2-benzyl-6-methoxyindan-1-ylidene) acetonitrile, the title compound was synthesized in otherwise the same manner as Reference Example 9 (yield 69%, oil).

NMR(d$_6$-DMSO) δ: 2.32–3.30(9H,m), 3.76(3H,s), 5.97 (1H,t, J=6.8 Hz), 6.75(1H,dd,J=2.4 Hz,8.2 Hz), 7.01(1H,d, J=2.4 Hz), 7.08–7.40(6H,m).

Reference Example 19

2-(2-Benzyl-5-methoxy-1H-inden-3-yl)ethylamine hydrochloride

Using (E)-2-(2-benzyl-6-methoxyindan-1-ylidene) ethylamine, the procedure of Reference Example 14 was otherwise repeated to provide the title compound (yield 74%).

m.p. 217–219° C. (as recrystallized from ethanol) NMR (d$_6$-DMSO) δ: 2.96(4H,br s), 3.15(2H,s), 3.79(3H,s), 3.82 (2H,s), 6.68(1H,dd,J=2.2 Hz,8.1 Hz), 7.06(1H,d,J=2.2 Hz), 7.15–7.40(6H,m), 8.13(2H,br s).

Reference Example 20

Ethyl (E)-3-(3-Fluoro-4-methoxyphenyl)acrylate

To a suspension of 60% sodium hydride (5.7 g, 154 mmol) in tetrahydrofuran (150 ml) was added triethyl phosphonoacetate (34.6 g, 154 mmol) dropwise under ice-cooling and the mixture was stirred for about 20 minutes until hydrogen had ceased to evolve and the reaction mixture become homogeneous. To this reaction mixture was added a solution of 3-fluoro-4-methoxybenzaldehyde (19.8 g, 128 mmol) in tetrahydrofuran (30 ml) dropwise and the mixture was stirred at room temperature for 3 hours. This reaction mixture was poured in water and extracted with ethyl acetate. The extract was washed serially with saturated saline and water and dried over anhydrous magnesium sulfate and the solvent was distilled off under reduced pressure. The residue was purified by silica gel column chromatography (ethyl acetate-hexane=1:1) to provide the title compound (yield 28.8 g, quantitative).

m.p. 39–41° C. NMR(CDCl$_3$) δ: 1.34(3H,t,J=7.1 Hz), 3.93(3H,s), 4.26(2H,q,J=7.1 Hz), 6.30(1H,d,J=16 Hz), 6.96 (1H,t,J=8.6 Hz), 7.21–7.33(2H,m), 7.59(1H,d,J=16 Hz). Elemental analysis for C$_{12}$H$_{13}$FO$_3$: Calcd.: C, 64.28; H, 5.84; F, 8.47. Found: C, 64.33; H, 5.74; F, 8.32.

Reference Example 21

Ethyl 3-(3-fluoro-4-methoxyphenyl)propionate

Starting with ethyl (E)-3-(3-fluoro-4-methoxyphenyl) acrylate, the title compound was synthesized in otherwise the same manner as Reference Example 16 (quantitative; oil).

NMR(CDCl$_3$) δ: 1.24(3H,t,J=7.2 Hz), 2.58(2H,t,J=7.5 Hz), 2.88(2H,t,J=7.5 Hz), 3.87(3H,s), 4.13(2H,q,J=7.2 Hz), 6.82–6.98(3H,m).

Reference Example 22

3-(3-Fluoro-4-methoxyphenyl)propionic acid

To a solution of ethyl 3-(3-fluoro-4-methoxyphenyl) propionate (29.1 g, 129 mmol) in ethanol(50 ml)-water(50 ml) was added potassium hydroxide (9.4 g, 167 mmol) and the mixture was stirred at 80° C. for 1 hour. After cooling, the reaction mixture was poured in diluted hydrochloric acid and the resulting crystals were recovered by filtration and washed with diethyl ether to provide the title compound (yield 24.4 g, 96%).

m.p. 116–119° C. NMR(CDCl$_3$) δ: 2.65(2H,t,J=7.5 Hz), 2.89(2H,t,J=7.5 Hz), 3.87(3H,s), 6.80–7.00(3H,m). Elemental analysis for C$_{10}$H$_{11}$FO$_3$: Calcd.: C, 60.60; H, 5.59. Found: C, 60.49; H, 5.43.

Reference Example 23

5-Fluoro-6-methoxy-1-indanone

Starting with 3-(3-fluoro-4-methoxyphenyl)propionic acid, the title compound was synthesized in otherwise the same manner as Reference Example 11 (yield 94%).

m.p. 152–154° C. NMR(CDCl$_3$) δ: 2.70(2H,t,J=5.5 Hz), 3.07(2H,t,J=5.5 Hz), 3.91(3H,s), 7.17(1H,d,J=10.3 Hz), 7.29(1H,d,J=10.3 Hz). Elemental analysis for C$_{10}$H$_9$FO$_2$: Calcd.: C, 66.66; H, 5.03. Found: C, 66.85; H, 4.97.

Reference Example 24

(E)-(5-Fluoro-6-methoxyindan-1-ylidene)acetonitrile

Starting with 5-fluoro-6-methoxy-1-indanone and diethyl cyanomethylphosphate, the title compound was synthesized in otherwise the same manner as Reference Example 8 (yield 73%).

m.p. 197–199° C. NMR(CDCl$_3$) δ: 3.00–3.19(4H,m), 3.91(3H,s), 5.52(1H,br s), 6.99–7.10(2H,m).

Reference Example 25

(E)-2-(5-Fluoro-6-methoxyindan-1-ylidene)ethylamine

Starting with (E)-(5-fluoro-6-methoxyindan-1-ylidene) acetonitrile, the title compound was synthesized in otherwise the same manner as Reference Example 9 (yield 85%; oil).

Reference Example 26

2-(6-Fluoro-5-methoxy-1H-inden-3-yl)ethylamine hydrochloride.

Starting with (E)-2-(5-fluoro-6-methoxyindan-1-ylidene) ethylamine, the title compound was synthesized in otherwise the same manner as Reference Example 19 (yield 71%).

m.p. 207–210° C. NMR(d$_6$-DMSO) δ: 2.87(2H,t,J=7.4 Hz), 3.00–3.17(2H,m), 3.29(2H,s), 3.90(3H,s), 6.40(1H,s), 7.27(1H,d,J=8.1 Hz), 7.33(1H,d,J=11.1 Hz), 8.15(2H,br s).

Working Example 1

2,2,2-Trifluoro-N-[2-(5-methoxy-2-phenyl-1H-inden-3-yl)ethyl]acetamide

To a solution of 2-(5-methoxy-2-phenyl-1H-inden-3-yl) ethylamine hydrochloride (0.2 g, 0.67 mmol.) and triethylamine (0.34 g, 3.33 mmol.) in a mixture of tetrahydrofuran (2 ml) and chloroform (2 ml) was added dropwise gradually trifluoroacetic anhydride (0.28 g, 1.33 mmol.) under ice-cooling. The mixture was stirred for 20 minutes, then the reaction mixture was poured into water, followed by extracting the organic substance with ethyl acetate. The extract solution was washed with a saturated aqueous saline solution and water, which was dried over anhydrous magnesium sulfate, followed by distilling off the solvent under reduced pressure. The residue was purified by means of a silica gel column chromatography (ethyl acetate:hexane=1:4) to give the titled compound (0.22 g, yield 92%), m.p.138–139° C. (recrystallized from ethyl acetate/hexane).

NMR(CDCl$_3$) δ: 3.03(2H,t,J=7.2 Hz), 3.61(2H,q,J=7.2 Hz), 3.71(2H,s), 3.88(3H,s), 6.29(1H,br s), 6.81(1H,dd,J=2.2&8.4 Hz), 7.03(1H,d,J=2.2 Hz), 7.39(1H,d,J=8.4 Hz), 7.40(5H,s). Elemental analysis for C$_{20}$H$_{18}$F$_3$NO$_2$: Calcd.: C, 66.48; H, 5.02; N, 3.88. Found: C, 66.23; H, 4.90; N, 3.65.

Working Example 2

2,2,2-Trifluoro-N-(2-(5-methoxy-1H-inden-3-yl) ethyl]acetamide

To a solution of (E)-2-(6-methoxyindan-1-ylidene) ethylamine (0.4 g, 2.11 mmol.), trifluoroacetic anhydride (0.53 g, 2.53 mmol.) and trifluoroacetic acid (0.48 g, 4.22 mmol.) in dichloromethane (20 ml) was added triethylamine (0.85 g, 8.44 mmol.) dropwise gradually under ice-cooling. The mixture was stirred for one hour at room temperature, then the reaction mixture was poured into water. The organic substance was extracted with chloroform. The extract solution was washed with a saturated aqueous saline solution and water, which was dried over anhydrous magnesium sulfate, followed by distilling off the solvent under reduced pressure. The residue was purified by means of a silica gel column chromatography (ethyl acetate:hexane=15:85), followed by recrystallization from isopropyl ether/hexane to afford the titled compound (yield 0.20 g, 33%), m.p.87–88° C. (recrystallized from isopropyl ether/hexane).

NMR(CDCl$_3$) δ: 2.84(2H,dt,J=1.2&6.6 Hz), 3.32(2H,d, J=6.6 Hz), 3.70(2H,q,J=6.6 Hz), 3.85(3H,s), 6.33(1H,br s), 6.40(1H,br s), 6.80(1H,dd,J=2.2&8.2 Hz), 6.91(1H,d,J=2.2 Hz), 7.36(1H,d,J=8.2 Hz). Elemental analysis for C$_{14}$H$_{14}$F$_3$NO$_2$: Calcd.: C, 58.95; H, 4.95; N, 4.91. Found: C, 58.89; H, 4.94; N, 5.08.

Working Example 3

2,2,2-Trifluoro-N-[3-(7-methoxy-3,4-dihydronaphthalen-1-yl)propyl]acetamide

In substantially the same manner as in Working Example 1, the titled compound was produced by the reaction of 3-(7-methoxy-3,4-dihydronaphthalen-1-yl) propylamine with trifluoroacetic anhydride (yield 87%, oily).

NMR(CDCl$_3$) δ: 1.84(2H,m), 2.16–2.30(2H,m), 2.50(2H, t,J=6.8 Hz), 2.67(2H,t,J=7.9 Hz), 3.40(2H,q,J=6.6 Hz), 3.80 (3H,s), 5.91(1H,t,J=4.6 Hz), 6.35(1H,br s), 6.70(1H,dd,J= 2.8&8.2 Hz), 6.77(1H,d,J=2.8 Hz), 7.07(1H,d,J=8.2 Hz). Elemental analysis for C$_{16}$H$_{18}$F$_3$NO$_2$: Calcd.: C, 61.34; H, 5.79; N, 4.47; F, 18.19. Found: C, 61.22; H, 5.77; N, 4.63; F, 18.22.

Working Example 4

N-[3-(7-methoxy-3,4-dihydronaphthalen-1-yl) propyl]acetamide

In substantially the same manner as in Working Example 1, the titled compound was produced by allowing 3-(7- methoxy-3,4-dihydronaphthalen-1-yl)propylamine to react with acetyl chloride (yield 90%, oily).

NMR(CDCl$_3$) δ: 1.75(2H,m), 1.95(3H,s), 2.13–2.30(2H, m), 2.46(2H,t,J=7.4 Hz), 2.66(2H,t,J=7.9 Hz), 3.29(2H,q,J= 6.5 Hz), 3.80(3H,s), 5.50(1H,br s), 5.89(1H,t,J=4.4 Hz), 6.69(1H,dd,J=2.2&8.1 Hz), 6.79(1H,d,J=2.2 Hz), 7.07(1H, d,J=8.1 Hz). Elemental analysis for C$_{16}$H$_{21}$NO$_2$: Calcd.: C, 74.10; H, 8.16; N, 5.40. Found: C, 74.23; H, 8.21; N, 5.33.

Working Example 5

N-[4-(7-methoxy-3,4-dihydronaphthalen-1-yl)butyl] acetamide

In substantially the same manner as in Working Example 1, the titled compound was produced by allowing 4-(7-methoxy-3,4-dihydronaphthalen-1-yl)butylamine to react with acetyl chloride (yield 95%), m.p.79–81° C. (recrystallized from ethyl acetate/hexane).

NMR(CDCl$_3$) δ: 1.49–1.62(4H,m), 1.95(3H,s), 2.14–2.30 (2H,m), 2.36–2.50(2H,m), 2.66(2H,t,J=8.1 Hz), 3.20–3.33 (2H,m), 3.80(3H,s), 5.44(1H,br s), 5.87(1H,t,J=4.4 Hz), 6.68(1H,dd,J=2.4&8.2 Hz), 6.80(1H,d,J=2.4 Hz), 7.06(1H, d,J=8.2 Hz). Elemental analysis for C$_{17}$H$_{23}$NO$_2$: Calcd.: C, 74.69; H, 8.48; N, 5.12. Found: C, 74.66; H, 8.30; N, 5.01.

Working Example 6

2,2,2-Trifluoro-N-[4-(7-methoxy-3,4-dihydronaphthalen-1-yl)butyl]acetamide

Starting with 4-(7-methoxy-3,4-dihydronaphthalen-1-yl) butylamine and trifluoroacetic anhydride, the title compound was synthesized in otherwise the same manner as Example 1 (yield 97%; oil).

NMR(CDCl$_3$) δ: 1.40–1.70(4H,m), 2.15–2.30(2H,m), 2.38–2.55(2H,m), 2.67(2H,t,J=7.9 Hz), 3.30–3.42(2H,m), 3.80(3H,s), 5.87(1H,t,J=4.6 Hz), 6.27(1H,br s), 6.69(1H,dd, J=2.6 Hz,8.1 Hz), 6.78(1H,d,J=2.6 Hz), 7.07(1H,d,J=8.1 Hz). Elemental analysis for C$_{17}$H$_{20}$F$_8$NO$_2$: Calcd.: C, 62.38; H, 6.16; N, 4.28; F, 17.41. Found: C, 61.98; H, 6.14; N, 4.14; F, 17.45.

Working Example 7

N-[2-(5-Methoxy-1H-inden-3-yl)ethyl]acetamide

To a solution of (E)-2-(6-methoxyindan-1-ylidene)-ethylamine (736 mg, 3.89 mmol) and triethylamine (0.59 g, 5.84 mmol) in tetrahydrofuran (20 ml) was added acetyl chloride (0.37 g, 4.70 mmol) gradually dropwise on an ice bath and the mixture was stirred at room temperature for 2 hours. This reaction mixture was poured in water and extracted with ethyl acetate. The extract was washed serially with saturated saline and water and dried over anhydrous magnesium sulfate. Finally the solvent was distilled off under reduced pressure to provide (E)-N-[2-(6-methoxyindan-1-ylidene)ethyl]acetamide (yield 1.0 g, 90%).

The (E)-N-[2-(6-methoxyindan-1-ylidene)ethyl]-acetamide (1.0 g, 4.32 mmol) thus obtained was dissolved in trifluoroacetic acid(6 ml)-tetrahydrofuran(6 ml) and the solution was refluxed for 1.5 hours. This reaction mixture was poured in water and extracted with ethyl acetate. The extract was washed serially with saturated saline and water and dried over anhydrous magnesium sulfate and the solvent was distilled off under reduced pressure. The residue was purified by silica gel column chromatography (ethyl acetate-methanol=96:4) to provide the title compound (yield 0.9 g, 90%).

NMR (CDCl$_3$) δ: 1.96(3H,s), 2.76(2H,t,J=6.4 Hz), 3.30 (2H,s), 3.60(2H,q,J=6.4 Hz), 3.85(3H,s), 5.68(1H,br s), 6.31 (1H,s), 6.79(1H,dd,J=2.4 Hz,8.0 Hz), 6.94(1H,d,J=2.4 Hz), 7.35(1H,d,J=8.0 Hz).

Working Example 8

2,2,2-Trifluoro-N-[2-(6-bromo-5-methoxy-1H-inden-3-yl)-ethyl]acetamide

To a solution of 2-(6-bromo-5-methoxy-1H-inden-3-yl) ethylamide hydrochloride (1.2 g, 3.94 mmol) and triethylamine (1.2 g, 11.8 mmol) in tetrahydrofuran (20 ml) was added trifluoroacetic anhydride (0.99 g, 4.73 mmol) dropwise under ice-cooling and the mixture was stirred at room temperature for 2 hours. This reaction mixture was poured in water and extracted with ethyl acetate. The extract was washed serially with saturated saline and water and dried over anhydrous magnesium sulfate and the solvent was distilled off under reduced pressure. The residue was purified by silica gel column chromatography (ethyl acetate-hexane=15:85) and recrystallized from ethyl acetate-hexane to provide the title compound (yield 1.06 g, 74%).

m.p. 126–129° C. (as recrystallized from ethyl acetate-hexane); NMR(CDCl$_3$) δ: 2.80–2.91(2H,m), 3.32(2H,s), 3.70(2H,q, J=6.9 Hz), 3.95(3H,s), 6.33(1H,s), 6.46(1H,br s), 6.95(1H,s), 7.63(1H,s). Elemental analysis for C$_{14}$H$_{13}$BrF$_3$NO$_2$: Calcd.: C, 46.18; H, 3.60; N, 3.85; Br, 21.94; F, 15.65. Found: C, 46.06; H, 3.49; N, 3.75; Br, 21.78; F, 15.58.

Working Example 9

N-[2-(6-Bromo-5-methoxy-1H-inden-3-yl)ethyl] acetamide

Starting with 2-(6-bromo-5-methoxy-1H-inden-3-yl) ethylamine hydrochloride and acetyl chloride, the title compound was synthesized in otherwise the same manner as Example 8 (yield 83%).

m.p. 146–148° C. (as recrystallized from ethyl acetate) NMR(CDCl$_3$) δ: 1.97(3H,s), 2.71–2.84(2H,m), 3.27–3.34 (2H,m), 3.58(2H,q,J=7.0 Hz), 3.95(3H,s), 5.62(1H,br s), 6.31(1H,t,J=1.7 Hz), 6.99(1H,s), 7.61(1H,s). Elemental analysis for C$_{14}$H$_{16}$BrNO$_2$: Calcd.: C, 54.21; H, 5.20; N, 4.52; Br, 25.76. Found: C, 54.16; H, 5.23; N, 4.67; Br, 25.77.

Working Example 10

N-[2-(6-Bromo-5-methoxy-1H-inden-3-yl)ethyl] propionamide

Starting with 2-(6-bromo-5-methoxy-1H-inden-3-yl) ethylamine hydrochloride and propionyl chloride, the title compound was synthesized in otherwise the same manner as Example 8 (yield 95%).

m.p. 106–109° C. (as recrystallized from ethyl acetate-hexane); NMR(CDCl$_3$) δ: 1.15(3H,t,J=7.6 Hz), 2.19(2H,q, J=7.6 Hz), 2.77(2H,dt,J=1.4 Hz,7.0 Hz), 3.29(2H,d,J=1.8 Hz), 3.60(2H,q,J=6.9 Hz), 3.95(3H,s), 5.60(1H,br s), 6.31 (1H,s), 6.98(1H,s), 7.61(1H,s). Elemental analysis for C$_{15}$H$_{18}$BrNO$_2$: Calcd.: C, 55.57; H, 5.60; N, 4.32; Br, 24.65. Found: C, 55.55; H, 5.68; N, 4.07; Br, 24.78.

Working Example 11

2,2,2-Trifluoro-N-[2-(2-benzyl-5-methoxy-1H-inden-3-yl)ethyl]acetamide

Starting with 2-(2-benzyl-5-methoxy-1H-inden-3-yl) ethylamine hydrochloride and trifluoroacetic anhydride, the title compound was synthesized in otherwise the same manner as Example 8 (yield 95%).

m.p. 126–128° C. (as recrystallized from ethyl acetate-hexane) NMR(CDCl$_3$) δ: 2.93(2H,t,J=7.1 Hz), 3.23(2H,s), 3.60(2H,q,J=7.1 Hz), 3.80(2H,s), 3.85(3H,s), 6.45(1H,br s), 6.72(1H,dd,J=2.4 Hz,8.1 Hz), 6.92(1H,d,J=2.4 Hz), 7.12–7.37(6H,m). Elemental analysis for C$_{21}$H$_{20}$F$_3$NO$_2$ Calcd.: C, 67.19; H, 5.37; N, 3.73. Found: C, 67.22; H, 5.35; N, 3.45.

Working Example 12

N-[2-(2-Benzyl-5-methoxy-1H-inden-3-yl)ethyl]acetamide

Starting with 2-(2-benzyl-5-methoxy-1H-inden-3-yl)ethylamine hydrochloride and acetyl chloride, the title compound was synthesized in otherwise the same manner as Example 8 (yield 94%).

m.p. 133–135° C. (as recrystallized from ethyl acetate-hexane); NMR(CDCl$_3$) δ: 1.87(3H,s), 2.85(2H,t,J=6.6 Hz), 3.22(2H,s), 3.50(2H,q,J=6.6 Hz), 3.82(2H,s), 3.84(3H,s), 5.52(1H,br s), 6.70(1H,dd,J=2.2 Hz,8.1 Hz), 6.94(1H,d,J=2.2 Hz), 7.12–7.34(6H,m). Elemental analysis for C$_{21}$H$_{23}$NO$_2$: Calcd.: C, 78.47; H, 7.21; N, 4.36. Found: C, 78.30; H, 7.04; N, 4.32.

Working Example 13

N-[2-(2-Benzyl-5-methoxy-1H-inden-3-yl)ethyl]propionamide

Starting with 2-(2-benzyl-5-methoxy-1H-inden-3-yl)ethylamine hydrochloride and propionyl chloride, the title compound was synthesized in otherwise the same manner as Example 8 (yield 98%).

m.p. 149–151° C. (as recrystallized from ethyl acetate-hexane); NMR(CDCl$_3$) δ: 1.10(3H,t,J=7.6 Hz), 2.10(2H,q,J=7.6 Hz), 2.86(2H,t,J=7.0 Hz), 3.22(2H,s), 3.51(2H,q,J=7.0 Hz), 3.82(2H,s), 3.84(3H,s), 5.52(1H,br s), 6.70(1H,dd,J=2.4 Hz,8.1 Hz), 6.95(1H,d,J=2.4 Hz), 7.13–7.39(6H,m). Elemental analysis for C$_{22}$H$_{26}$NO$_2$: Calcd.: C, 78.77; H, 7.51; N, 4.18. Found: C, 78.79; H, 7.46; N, 4.29.

Working Example 14

N-[2-(2-Benzyl-5-methoxy-1H-inden-3-yl)ethyl]butyramide

Starting with 2-(2-benzyl-5-methoxy-1H-inden-3-yl)ethylamine hydrochloride and butyryl chloride, the title compound was synthesized in otherwise the same manner as Example 8 (yield 97%).

m.p. 127–129° C. (as recrystallized from ethyl acetate-hexane); NMR(CDCl$_3$) δ: 0.91(3H,t,J=7.3 Hz), 1.50–1.70 (2H,m), 2.04(2H,t,J=7.5 Hz), 2.86(2H,t,J=7.0 Hz), 3.22(2H, s), 3.51(2H,q,J=7.0 Hz), 3.82(2H,s), 3.85(3H,s), 5.51(1H,br s), 6.70(1H,dd,J=2.4 Hz,8.1 Hz), 6.95(1H,d,J=2.4 Hz), 7.12–7.35(6H,m). Elemental analysis for C$_{23}$H$_{27}$NO$_2$: Calcd.: C, 79.05; H, 7.79; N, 4.01. Found: C, 78.93; H, 7.83; N, 3.93.

Working Example 15

N-[2-(5-Methoxy-1H-inden-3-yl)ethyl]propionamide

Using (E)-2-(6-methoxyindan-1-ylidene)ethylamine, the procedure of Reference Example 14 was otherwise repeated to provide 2-(5-methoxy-1H-inden-3-yl)ethylamine hydrochloride. Then, starting with this 2-(5-methoxy-1H-inden-3-yl)ethylamine hydrochloride and propionyl chloride, the title compound was synthesized in otherwise the same manner as Example 8 (yield 86%).

m.p. 61–63° C. (as recrystallized from ethyl acetate-hexane); NMR(CDCl$_3$) δ: 1.14(3H,t,J=7.5 Hz), 2.18(2H,q, J=7.5 Hz), 2.76(2H,dt,J=1.4 Hz,6.6 Hz), 3.30(2H,d,J=1.8 Hz), 3.61(2H,q,J=6.6 Hz), 3.85(3H,s), 5.55(1H,br s), 6.31 (1H,s), 6.78(1H,dd,J=2.2 Hz,8.1 Hz), 6.93(1H,d,J=2.2 Hz), 7.35(1H,d,J=8.1 Hz). Elemental analysis for C$_{15}$H$_{18}$NO$_2$: Calcd.: C, 73.44; H, 7.81; N, 5.71. Found: C, 73.24; H, 7.74; N, 5.85.

Working Example 16

N-[2-(5-Methoxy-1H-inden-3-yl)ethyl]butyramide

Starting with 2-(6-methoxyindan-1-ylidene)ethylamine (hydrochloride) and butyryl chloride, the title compound was synthesized in otherwise the same manner as Example 15 (yield 65%).

m.p. 64–67° C. NMR (CDCl$_3$) δ: 0.93(3H,t,J=7.3 Hz), 1.58–1.74(2H,m), 2.13(2H,t,J=7.5 Hz), 2.76(2H,t,J=7.0 Hz), 3.30(1H,br s), 3.61(2H,q,J=6.4 Hz), 5.55(1H,br s), 6.31(1H,br s), 6.78(1H,dd,J=2.4 Hz,8.1 Hz), 6.93(1H,d,J= 2.4 Hz), 7.35(1H,d,J=8.1 Hz). Elemental analysis for C$_{16}$H$_{21}$NO$_2$: Calcd.: C, 74.10; H, 8.16; N, 5.40. Found: C, 74.31; H, 8.04; N, 5.42.

Working Example 17

N-[2-(6-Fluoro-5-methoxy-1H-inden-3-yl)ethyl]propionamide

Starting with 2-(6-fluoro-5-methoxy-1H-inden-3-yl)ethylamine hydrochloride and propionyl chloride, the title compound was synthesized in otherwise the same manner as Example 8 (yield 83%).

m.p. 140–143° C. (as recrystallized from ethyl acetate) NMR(CDCl$_3$) δ: 1.15(3H,t,J=7.5 Hz), 2.19(2H,q,J=7.5 Hz), 2.76(2H,dt,J=1.5 Hz,7.0 Hz), 3.29(2H,d,J=1.8 Hz), 3.60(2H, q,J=7.0 Hz), 3.94(3H,s), 5.59(1H,br s), 6.26(1H,br s), 7.00 (1H,d,J=8.1 Hz), 7.19(1H,d,J=10.6 Hz). Elemental analysis for C$_{15}$H$_{18}$FNO$_2$: Calcd.: C, 68.42; H, 6.89; N, 5.32. Found: C, 68.64; H, 6.84; N, 5.25.

Working Example 18

N-[2-(6-Fluoro-5-methoxy-1H-inden-3-yl)ethyl]butyramide

Starting with 2-(6-fluoro-5-methoxy-1H-inden-3-yl)ethylamine hydrochloride and butyryl chloride, the title compound was synthesized in otherwise the same manner as Example 8 (yield 80%).

m.p. 90–92° C. (as recrystallized from ethyl acetate-hexane); NMR (CDCl$_3$) δ: 0.94(3H,t,J=7.3 Hz), 1.65(2H, m), 2.14(2H, t,J=7.5 Hz), 2.75(2H,dt,J=1.5 Hz,7.0 Hz), 3.29(2H,br s), 3.60(2H,q,J=6.6 Hz), 3.94(3H,s), 5.60(1H,br s), 6.26(1H,br s), 7.00(1H,d,J=8.1 Hz), 7.19(1H,d,J=11.0 Hz). Elemental analysis for C$_{16}$H$_{20}$FNO$_2$: Calcd.: C, 69.29; H, 7.27; N, 5.05. Found: C, 69.19; H, 7.26; N, 5.16.

In Table 1, structural formulae of the compounds obtained in Working Examples 1 to 18 are shown.

TABLE 1

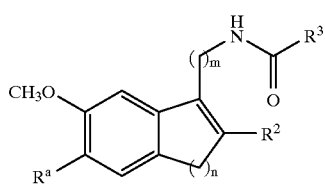

| Working Ex. No. | $R^a$ | $R^2$ | $R^3$ | m | n |
|---|---|---|---|---|---|
| 1 | H | $C_6H_5$ | $CF_3$ | 2 | 1 |
| 2 | H | H | $CF_3$ | 2 | 1 |
| 3 | H | H | $CF_3$ | 3 | 2 |
| 4 | H | H | $CH_3$ | 3 | 2 |
| 5 | H | H | $CH_3$ | 4 | 2 |
| 6 | H | H | $CF_3$ | 4 | 2 |
| 7 | H | H | $CH_3$ | 2 | 1 |
| 8 | Br | H | $CF_3$ | 2 | 1 |
| 9 | Br | H | $CH_3$ | 2 | 1 |
| 10 | Br | H | $C_2H_5$ | 2 | 1 |
| 11 | H | benzyl | $CF_3$ | 2 | 1 |
| 12 | H | benzyl | $CH_3$ | 2 | 1 |
| 13 | H | benzyl | $C_2H_5$ | 2 | 1 |
| 14 | H | benzyl | $C_3H_7$ | 2 | 1 |
| 15 | H | H | $C_2H_5$ | 2 | 1 |
| 16 | H | H | $C_3H_7$ | 2 | 1 |
| 17 | F | H | $C_2H_5$ | 2 | 1 |
| 18 | F | H | $C_3H_7$ | 2 | 1 |

| Formulation Example 1 | |
|---|---|
| (1) Compound obtained in Working Example 1 | 10.0 g |
| (2) Lactose | 60.0 g |
| (3) Corn starch | 35.0 g |
| (4) Gelatin | 3.0 g |
| (5) Magnesium stearate | 2.0 g |

A mixture of 10.0 g of the compound obtained in Working Example 1, 60.0 g of lactose and 35.0 g of corn starch was granulated through a sieve of 1 mesh, using 30 ml of an aqueous solution of 10 weight % gelatin (3.0 g in terms of gelatin). The granular product was dried at 40° C., which was subjected to sieving again. The granules thus-obtained were blended with 2.0 g of magnesium stearate, and the mixture was subjected to compression. The core tablet thus obtained was sugar-coated with an aqueous suspension containing sucrose, titanium dioxide, talc and gum arabic. The coated tablets were polished with beeswax to prepare 1000 tablets.

| Formulation Example 2 | |
|---|---|
| (1) Compound obtained in Working Example 1 | 10.0 g |
| (2) Lactose | 70.0 g |
| (3) Corn starch | 50.0 g |
| (4) Soluble starch | 7.0 g |
| (5) Magnesium stearate | 3.0 g |

With 70 ml of an aqueous solution of soluble starch (7.0 g in terms of soluble starch), 10.0 g of the compound obtained in Working Example 1 and 3.0 g of magnesium stearate were granulated and dried, followed by blending with 70.0 g of lactose and 50.0 g of corn starch. The mixture was subjected to compression to prepare 1000 tablets.

Experimental Example 1

Action of inhibiting 2-[$^{125}$I]iodomelatonin binding

The forebrains of 7-day-old chickens (white leghorn) were homogenized with ice-cooled assay-buffer (50 mM Tris-HCl, pH 7.7, at 25° C.) and centrifuged at 44,000×g for 10 minutes to give pellet. The pellet was washed once with the same buffer solution, which was further homogenized with the assay-buffer to make a protein concentration of 0.3–0.4 mg/mL. The homogenate was used as a membrane sample. In a test tube, the membrane sample and a ligand (80 pM 2-[$^{125}$I]iodomelatonin, ca. 100,000 dpm) were mixed to make the whole volume 0.5 mL. The mixture was incubated for 90 minutes at 25° C., to which was added 3 mL of ice-cooled assay buffer, immediately followed vacuum filtration on Whatman GF/B which was further washed twice with 3 mL each of ice-cold assay buffer. The radioactivity on the filter was determined by means of gamma-counter. Specific binding was calculated by subtracting the non-specific binding which was determined in the presence of 10 μM melatonin. The 50% inhibiting concentration (IC$_{50}$) was determined by the log-probit analysis.

TABLE 2

| Action of inhibiting 2-[$^{125}$I] iodomelatonin | |
|---|---|
| Working Example No. | IC$_{50}$ (nM) |
| 1 | 0.087 |

From the results shown in Table 2, it is considered that the compound (I) of the present invention and the compound (I$^a$) have an excellent binding affinity for melatonin receptor, especially melatonin receptor agonistic activity.

INDUSTRIAL APPLICABILITY

Since the compound (I) of the present invention and the compound (I$^a$) show excellent binding affinity for melatonin receptor, they can provide clinically useful prophylactic and therapeutic agents of diseases related with the action of melatonin in living bodies. And, the compound (I) of the present invention and the compound (I$^a$) are excellent also in the behavior in living bodies.

We claim:

1. A compound of the formula:

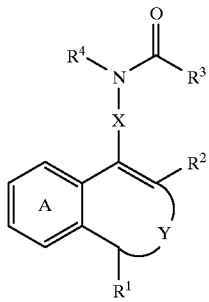

wherein $R^1$ represents i) hydrogen or ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy;

$R^2$ represents (i) hydrogen, (ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy or (iii) a 5- to 10-membered heterocyclic group containing, besides carbon atoms, 1 to 3 hetero atoms selected from nitrogen atom, oxygen atom and sulfur atom, which group may be substituted by 1 to 5 substituents selected from the group consisting of halogen, $C_{1-6}$ alkyl, $C_{3-6}$ cycloalkyl, $C_{2-6}$ alkynyl, $C_{2-6}$ alkenyl, $C_{7-11}$ aralkyl, $C_{6-10}$ aryl, $C_{1-6}$ alkoxy, $C_{6-10}$ aryloxy, $C_{1-6}$ alkyl-carbonyl, $C_{1-6}$ alkyl-carbonyloxy, carboxyl, $C_{1-6}$ alkoxy-carbonyl, carbamoyl, mono-, di- or tri-halogeno-$C_{1-4}$ alkyl, oxo, amindino, imino, amino, mono-$C_{1-4}$ alkylamino, di-$C_{1-4}$ alkylamino, 3- to 6-membered cyclic amino, $C_{1-3}$ alkylenedioxy, hydroxyl, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{1-6}$ alkylsulfinyl and $C_{1-6}$ alkylsulfonyl;

$R^3$ represents (i) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy, (ii) an amino group which may be substituted by 1 or 2 substituents selected from the group consisting of $C_{1-6}$ alkyl, $C_{2-6}$ alkenyl, $C_{2-6}$ alkynyl, $C_{3-6}$ cycloalkyl and $C_{6-14}$ aryl group, each of which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy or (iii) a hydroxyl group substituted by a $C_{1-6}$ alkyl, $C_{2-6}$ alkenyl, $C_{2-6}$ alkynyl, $C_{3-6}$ cycloalkyl or $C_{6-14}$ aryl group, each of which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy;

$R^4$ represents (i) hydrogen or (ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkylcarbonyl, $C_{1-6}$ alkoxycarbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy;

ring A represents a benzene ring substituted by 1 to 3 substituents selected from the group consisting of (i) halogen, (ii) hydroxyl, (iii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy, (iv) an amino group which may be substituted by 1 or 2 substituents selected from the group consisting of a $C_{1-6}$ alkyl, $C_{2-6}$ alkenyl, $C_{2-6}$ alkynyl, $C_{3-6}$ cycloalkyl and $C_{6-14}$ aryl group, each of which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy, (v) a mercapto group which may be substituted by a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy, (vi) a hydroxyl group substituted by a $C_{1-6}$ alkyl, $C_{2-6}$ alkenyl, $C_{2-6}$ alkynyl, $C_{3-6}$ cycloalkyl or $C_{6-14}$ aryl group, each of which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy, (vii) a $C_{1-6}$ acylamino group and (viii) a $C_{1-3}$ alkylenedioxy group;

X represents a straight $C_{2-4}$ alkylene group which may be substituted by 1 to 3 substituents selected from the group consisting of (i) a $C_{1-6}$ alkyl, $C_{2-6}$ alkenyl, $C_{2-6}$ alkynyl, $C_{3-6}$ cycloalkyl or $C_{6-14}$ aryl group, each of which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy, (ii) halogen, (iii) nitro, (iv) cyano, (v) hydroxyl, (vi) $C_{1-6}$ alkoxy, (vii) amino, (viii) mono-$C_{1-6}$ alkylamino, (ix) di-$C_{1-6}$ alkylamino, (x) $C_{1-6}$ alkyl-carbonyl and (xi) $C_{6-10}$ aryloxy; and Y represent a bond, or a salt thereof.

2. A compound of claim 1 wherein $R^1$ is hydrogen or a $C_{1-6}$ alkyl group.

3. A compound of claim 1 wherein $R^2$ is (i) hydrogen, (ii) a $C_{6-14}$ aryl group which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy or (iii) a 5- and 6-membered heteroaromatic group which may be substituted by 1 to 3 substituents selected from the group consisting of halogen, $C_{1-6}$ alkyl, $C_{3-6}$ cycloalkyl, $C_{2-6}$ alkynyl, $C_{2-6}$ alkenyl, $C_{7-11}$ aralkyl, $C_{6-10}$ aryl, $C_{1-6}$ alkoxy, $C_{6-10}$ aryloxy, $C_{1-6}$ alkyl-carbonyl, $C_{1-6}$ alkyl-carbonyloxy, carboxyl, $C_{1-6}$ alkoxy-carbonyl, carbamoyl, mono-, di- or tri-halogeno-$C_{1-4}$ alkyl, oxo, amidino, imino, amino, mono-$C_{1-6}$ alkylamino, di-$C_{1-6}$ alkylamino, 3- to 6-membered cyclic amino, $C_{1-3}$ alkylenedioxy, hydroxyl, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{1-6}$ alkylsulfinyl, and $C_{1-6}$ alkylsulfonyl.

4. A compound of claim 1 wherein $R^3$ is a $C_{1-6}$ alkyl group which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy.

5. A compound of claim 1 wherein $R^4$ is hydrogen or a $C_{1-6}$ alkyl group.

6. A compound of claim 1 wherein ring A is a benzene ring substituted by 1 or 2 substituents selected from the group consisting of halogen and a $C_{1-6}$ alkoxy group.

7. A compound of claim 1 wherein ring A moiety is represented by the formula:

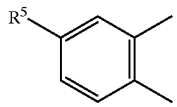

wherein $R^5$ represents a $C_{1-6}$ alkoxy group.

8. A compound of claim 1 wherein X is an ethylene group.
9. A compound of claim 1 wherein $R^1$ is hydrogen;
   $R^2$ is (i) hydrogen or (ii) a $C_{6-14}$ aryl or 5- or 6-membered heteroaromatic group which may be substituted by 1 to 3 substituents selected from the group consisting of halogen, $C_{1-6}$ alkoxy and $C_{6-10}$ aryl;
   $R^3$ is a $C_{1-6}$ alkyl group which may be substituted by 1 to 3 halogens;
   $R^4$ is hydrogen;
   ring A is a benzene ring substituted by 1 or 2 substituents selected from the group consisting of halogen and a $C_{1-6}$ alkoxy group; and
   X is an ethylene group.

10. A compound of claim 1 wherein $R^1$ is hydrogen;
    $R^2$ is hydrogen, a $C_{6-10}$ aryl group or a $C_{6-10}$ aryl-$C_{1-4}$ alkyl group;
    $R^3$ is a $C_{1-6}$ alkyl group which may be substituted by 1 to 3 halogens;
    $R^4$ is hydrogen;
    ring A is a benzene ring substituted by 1 or 2 substituents selected from the group consisting of halogen and a $C_{1-6}$ alkoxy group; and
    X is a $C_{2-4}$ alkylene group.

11. A compound of claim 1 which is
    2,2,2-trifluoro-N-[2-(5-methoxy-2-phenyl-1H-inden-3-yl)ethyl]acetamide,
    N-[2-(5-methoxy-1H-inden-3-yl)ethyl]propionamide, or
    N-[2-(5-methoxy-1H-inden-3-yl)ethyl]butyramide.

12. A process for producing the compound of claim 1, which comprises reacting a compound of (i) the formula:

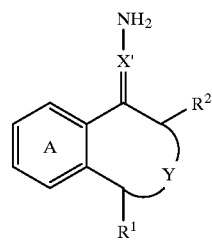

wherein X' represents a trivalent group formed by removing one hydrogen atom from the group represented by X, or (ii) the formula:

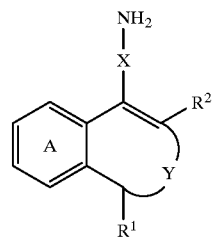

or a salt thereof,
   with a carboxylic acid, a salt or a reactive derivative thereof, or with an isocyanate.

13. A pharmaceutical composition which comprises a compound of claim 1, together with a pharmaceutically acceptable carrier.

14. A composition of claim 13 which has a binding affinity for melatonin receptor.

15. Method of regulating circadian rhythm comprising administering to a human the composition of claim 14.

16. Method of regulating sleep-awake rhythm comprising administering to a human the composition of claim 14.

17. Method of regulating time zone change syndrome comprising administering to a human the composition of claim 14.

18. Method of treating sleep disorders comprising administering to a human the composition of claim 13.

19. Method for treating diseases related to the action of melatonin in mammals which comprises administering to a subject in need a therapeutically effective amount of a compound of the formula:

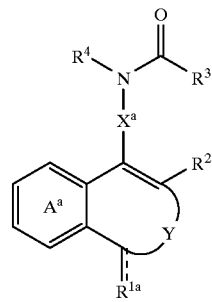

wherein ------ represents a single bond or a double bond;
   $R^{1a}$ represents 1) hydrogen or ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkylcarbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy;

$R^2$ represents (i) hydrogen, (ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy or (iii) a 5- to 10-membered heterocyclic group containing, besides carbon atoms, 1 to 3 hetero atoms selected from nitrogen atom, oxygen atom and sulfur atom, which group may be substituted by 1 to 5 substituents selected from the group consisting of halogen, $C_{1-6}$ alkyl, $C_{3-6}$ cycloalkyl, $C_{2-6}$ alkynyl, $C_{2-6}$ alkenyl, $C_{7-11}$ aralkyl, $C_{6-10}$ aryl, $C_{1-6}$ alkoxy, $C_{6-10}$ aryloxy, $C_{1-6}$ alkylcarbonyl, $C_{1-6}$ alkyl-carbonyloxy, carboxyl, $C_{1-6}$ alkoxy-carbonyl, carbamoyl, mono-, di- or tri-halogeno-$C_{1-4}$ alkyl, oxo, amidino, imino, amino, mono-$C_{1-6}$ alkylamino, di-$C_{1-6}$ alkylamino, 3- to 6-membered cyclic amino, $C_{1-3}$ alkylenedioxy, hydroxyl, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{1-6}$ alkylsulfinyl and $C_{1-6}$ alkylsulfonyl;

$R^3$ represents (i) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy, (ii) an amino group which may be substituted by 1 or 2 substituents selected from the group consisting of a $C_{1-6}$ alkyl, $C_{2-6}$ alkenyl, $C_{2-6}$ alkynyl, $C_{3-6}$ cycloalkyl and $C_{6-14}$ aryl group, each of which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy or (iii) a hydroxyl group substituted by a $C_{1-6}$ alkyl, $C_{2-6}$ alkenyl, $C_{2-6}$ alkynyl, $C_{3-6}$ cycloalkyl or $C_{6-14}$ aryl group, each of which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy;

$R^4$ represents (i) hydrogen or (ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkylcarbonyl, $C_{1-6}$ alkoxycarbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy;

ring $A^a$ represents a benzene ring which may be substituted by 1 to 3 substituents selected from the group consisting of (i) halogen, (ii) hydroxyl, (iii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy, (iv) an amino group which may be substituted by 1 or 2 substituents selected from the group consisting of a $C_{1-6}$ alkyl, $C_{2-6}$ alkenyl, $C_{2-6}$ alkynyl, $C_{3-6}$ cycloalkyl and $C_{6-14}$ aryl group, each of which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy, (v) a mercapto group which may be substituted by a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy, (vi) a hydroxyl group substituted by a $C_{1-6}$ alkyl, $C_{2-6}$ alkenyl, $C_{2-6}$ alkynyl, $C_{3-6}$ cycloalkyl or $C_{6-14}$ aryl group, each of which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy, (vii) a $C_{1-6}$ acylamino group and (viii) a $C_{1-3}$ alkylenedioxy group;

$X^a$ represents a straight $C_{1-6}$ alkylene group which may be substituted by 1 to 3 substituents selected from the group consisting of (i) a $C_{1-6}$ alkyl, $C_{2-6}$ alkenyl, $C_{2-6}$ alkynyl, $C_{3-6}$ cycloalkyl or $C_{6-14}$ aryl group, each of which may be substituted by 1 to 5 substituents selected from the group consisting of halogen, nitro, cyano, hydroxyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, mono-$C_{6-10}$ arylcarbamoyl, $C_{6-10}$ aryl and $C_{6-10}$ aryloxy, (ii) halogen, (iii) nitro, (iv) cyano, (v) hydroxyl, (vi) $C_{1-6}$ alkoxy, (vii) amino, (viii) mono-$C_{1-6}$ alkylamino, (ix) di-$C_{1-6}$ alkylamino, (x) $C_{1-6}$ alkyl-carbonyl and (xi) $C_{6-10}$ aryloxy; and Y represents a bond, or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 5,922,771
DATED : July 13, 1999
INVENTOR(S) : SHIGENORI OHKAWA ET AL.

It is certified that error appears in the above-identified patent and that said Letters Patent is hereby corrected as shown below:

ON THE TITLE PAGE [57] ABSTRACT

Line 8, "of" should read --for--; and
    Line 9, "with" should read --to--.

COLUMN 5

Line 12, "arallkyl" should read --aralkyl--.

COLUMN 7

Line 24, "Gamino," should read --amino,--.

COLUMN 9

Line 51, "Heterocyclic" should read --¶"Heterocyclic--;
    Line 52, "include," should read --includes--; and
    Line 62, "2-, 4-or" should read --2-, 4- or 5- --.

COLUMN 10

Line 24, "allkyl" should read --alkyl--.

COLUMN 12

Line 29, "include," should read --includes,--.

UNITED STATES PATENT AND TRADEMARK OFFICE
CERTIFICATE OF CORRECTION

PATENT NO. : 5,922,771
DATED : July 13, 1999
INVENTOR(S) : SHIGENORI OHKAWA ET AL.

It is certified that error appears in the above-identified patent and that said Letters Patent is hereby corrected as shown below:

COLUMN 13

Line 12, "dimethylamino)," should read --diethylamino),--;
    Line 31, "include," should read --includes--; and
    Line 56, "cyclopropyl" should read --cycloalkyl--.

COLUMN 14

Line 36, "preferred" should read --preferred are--.

COLUMN 15

Line 11, "R" should read --$R^3$--; and
    Line 38, "More" should read --A more--.

COLUMN 18

Line 15, "trilfuoro" should read --trifluoro--.

COLUMN 23

Line 31, "nitrites" should read --nitriles--.

COLUMN 24

Line 5, "nitrites" should read --nitriles--.

UNITED STATES PATENT AND TRADEMARK OFFICE
CERTIFICATE OF CORRECTION

PATENT NO.    :  5,922,771

DATED         :  July 13, 1999

INVENTOR(S)   :  SHIGENORI OHKAWA ET AL.

It is certified that error appears in the above-identified patent and that said Letters Patent is hereby corrected as shown below:

COLUMN 28

Line 18, "minutes" should read --minute--.

COLUMN 29

Line 5, "nitrites" should read --nitriles--; and
    Line 32, "hours" should read --hour--.

COLUMN 30

Line 48, "tO" should read --10--.

COLUMN 31

Line 3, "thereof." should read --thereof are preferred.--;
    Line 24, "sufloxide" should read --sulfoxide--; and
    Line 25, "them." should read --them are preferred.--.

COLUMN 32

Line 50, "carbon tetrachloride and 1,2-dichloroethane" should read --carbon tetrachloride, 1,2-dichloroethane--;
    Line 52, "sufloxide" should read --sulfoxide--.

UNITED STATES PATENT AND TRADEMARK OFFICE
CERTIFICATE OF CORRECTION

PATENT NO.    : 5,922,771
DATED         : July 13, 1999
INVENTOR(S)   : SHIGENORI OHKAWA ET AL.

It is certified that error appears in the above-identified patent and that said Letters Patent is hereby corrected as shown below:

COLUMN 33

Line 19, "bexane," should read --hexane--.

COLUMN 35

Line 37, "prepalations," should read --preparation,--.

COLUMN 36

Line 30, "lecitin," should read --lecithin,--;
    Line 31, "benzalconium" should read --benzalkonium--; and
    Line 58, "deviate" should read --deviate from--.

COLUMN 37

Line 6, "Herz" should read --Hertz--; and
    Line 52, "at 10 hours" should be deleted.

COLUMN 42

Line 44, "become" should read --had become--.

COLUMN 50

Line 7, "pellet." should read --a pellet.--; and
    Line 15, "followed" should read --followed by--.

UNITED STATES PATENT AND TRADEMARK OFFICE
CERTIFICATE OF CORRECTION

PATENT NO.    : 5,922,771
DATED         : July 13, 1999
INVENTOR(S)   : SHIGENORI OHKAWA ET AL.

It is certified that error appears in the above-identified patent and that said Letters Patent is hereby corrected as shown below:

<u>COLUMN 52</u>

Line 56, "represent" should read --represents--.

Signed and Sealed this

Eighth Day of February, 2000

Attest:

Q. TODD DICKINSON

*Attesting Officer*        *Commissioner of Patents and Trademarks*